(12) United States Patent
Liu et al.

(10) Patent No.: US 9,410,146 B2
(45) Date of Patent: Aug. 9, 2016

(54) COMPOSITIONS AND METHODS FOR RECOVERY OF NUCLEIC ACIDS OR PROTEINS FROM TISSUE SAMPLES FIXED IN CYTOLOGY MEDIA

(75) Inventors: Shubing Liu, Clarksville, MD (US); Suganthi Ramachandran, Fairfax, VA (US)

(73) Assignee: QIAGEN GAITHERSBURG INC., Gaithersburg, MD (US)

(*) Notice: Subject to any disclaimer, the term of this patent is extended or adjusted under 35 U.S.C. 154(b) by 867 days.

(21) Appl. No.: 12/881,531

(22) Filed: Sep. 14, 2010

(65) Prior Publication Data

US 2011/0065906 A1    Mar. 17, 2011

Related U.S. Application Data

(60) Provisional application No. 61/242,258, filed on Sep. 14, 2009, provisional application No. 61/253,300, filed on Oct. 20, 2009.

(51) Int. Cl.
*G01N 31/00* (2006.01)
*C07H 21/00* (2006.01)
*C12Q 1/68* (2006.01)
*C12N 15/10* (2006.01)
*C12N 1/06* (2006.01)
*C12Q 1/70* (2006.01)

(52) U.S. Cl.
CPC ............ *C12N 15/1003* (2013.01); *C12N 1/06* (2013.01); *C12N 15/1013* (2013.01); *C12Q 1/6806* (2013.01); *C12Q 1/708* (2013.01)

(58) Field of Classification Search
CPC ........... C12N 15/1003; C12N 15/1013; C12Q 1/6806; C12Q 1/6834
USPC ............................. 436/17; 435/6.1; 536/25.4
See application file for complete search history.

(56) References Cited

U.S. PATENT DOCUMENTS

| | | | |
|---|---|---|---|
| 4,486,536 A | 12/1984 | Baker et al. |
| 4,486,539 A | 12/1984 | Ranki et al. |
| 4,563,417 A | 1/1986 | Alabrella et al. |
| 4,563,419 A | 1/1986 | Ranki et al. |
| 4,689,294 A | 8/1987 | Boguslawski et al. |
| 4,731,325 A | 3/1988 | Palva et al. |
| 4,732,847 A | 3/1988 | Stuart et al. |
| 4,743,535 A | 5/1988 | Carrico |
| 4,751,177 A | 6/1988 | Stabinsky et al. |
| 4,775,619 A | 10/1988 | Urdea |
| 4,833,084 A | 5/1989 | Carrico |

(Continued)

FOREIGN PATENT DOCUMENTS

| | | |
|---|---|---|
| CN | 1690233 A | 11/2005 |
| CN | 101177701 A | 5/2008 |

(Continued)

OTHER PUBLICATIONS

Sheldock et al. BioTechniques 22:394-400 (Mar. 1997).*

(Continued)

*Primary Examiner* — Jezia Riley
(74) *Attorney, Agent, or Firm* — McBee Moore Woodward Vanik IP, LLC.

(57) ABSTRACT

The present invention provides compositions and methods for improving nucleic acid or protein recovery from fixed biological samples.

33 Claims, 9 Drawing Sheets

(56) References Cited

U.S. PATENT DOCUMENTS

| | | | |
|---|---|---|---|
| 4,851,330 A | 7/1989 | Kohne et al. | |
| 4,865,980 A | 9/1989 | Stuart et al. | |
| 4,868,105 A | 9/1989 | Urdea et al. | |
| 4,889,798 A | 12/1989 | Rabbani | |
| 4,894,325 A | 1/1990 | Englehardt et al. | |
| 5,082,830 A | 1/1992 | Brakel et al. | |
| 5,106,727 A | 4/1992 | Hartley et al. | |
| 5,116,734 A | 5/1992 | Higgs et al. | |
| 5,200,313 A * | 4/1993 | Carrico | 435/6.11 |
| 5,288,611 A | 2/1994 | Kohne et al. | |
| 5,374,524 A | 12/1994 | Miller et al. | |
| 5,424,413 A | 6/1995 | Hogan et al. | |
| 5,437,977 A | 8/1995 | Segev | |
| 5,474,895 A | 12/1995 | Ishii et al. | |
| 5,484,699 A | 1/1996 | Bouma et al. | |
| 5,545,806 A | 8/1996 | Lonberg et al. | |
| 5,545,807 A | 8/1996 | Surani et al. | |
| 5,556,748 A | 9/1996 | Douglas | |
| 5,614,362 A | 3/1997 | Urdea et al. | |
| 5,623,049 A | 4/1997 | Lobberding et al. | |
| 5,627,030 A | 5/1997 | Pandian et al. | |
| 5,629,153 A | 5/1997 | Urdea | |
| 5,629,156 A | 5/1997 | Shah et al. | |
| 5,635,352 A | 6/1997 | Urdea et al. | |
| 5,641,630 A | 6/1997 | Snitman | |
| 5,656,731 A | 8/1997 | Urdea | |
| 5,681,697 A | 10/1997 | Urdea et al. | |
| 5,681,897 A | 10/1997 | Silvis et al. | |
| 5,695,926 A | 12/1997 | Cros et al. | |
| 5,702,893 A | 12/1997 | Urdea et al. | |
| 5,728,531 A | 3/1998 | Yamada et al. | |
| 5,731,153 A | 3/1998 | Lucas et al. | |
| 5,735,315 A | 4/1998 | Petsche et al. | |
| 5,747,244 A | 5/1998 | Sheridan et al. | |
| 5,747,248 A | 5/1998 | Collins | |
| 5,750,338 A | 5/1998 | Collins et al. | |
| 5,759,773 A | 6/1998 | Tyagi et al. | |
| 5,786,183 A | 7/1998 | Ryder et al. | |
| 5,792,606 A | 8/1998 | Deger et al. | |
| 5,800,994 A | 9/1998 | Martinelli et al. | |
| 5,814,492 A | 9/1998 | Carrino et al. | |
| 5,821,339 A | 10/1998 | Schafer et al. | |
| 5,827,661 A | 10/1998 | Blais | |
| 5,853,993 A | 12/1998 | Dellinger et al. | |
| 5,888,724 A | 3/1999 | Silverstein et al. | |
| 5,981,179 A | 11/1999 | Lorincz et al. | |
| 5,994,079 A | 11/1999 | De La Rosa et al. | |
| 6,027,897 A | 2/2000 | Lorincz et al. | |
| 6,043,038 A | 3/2000 | Sivaraja et al. | |
| 6,057,099 A | 5/2000 | Nathan et al. | |
| 6,083,925 A | 7/2000 | Li et al. | |
| 6,110,676 A | 8/2000 | Coull et al. | |
| 6,110,682 A | 8/2000 | Dellinger et al. | |
| 6,110,687 A | 8/2000 | Nilsen | |
| 6,133,436 A * | 10/2000 | Koster et al. | 506/30 |
| 6,207,385 B1 | 3/2001 | Stanley | |
| 6,221,581 B1 | 4/2001 | Engelhardt et al. | |
| 6,225,053 B1 | 5/2001 | Garcia et al. | |
| 6,228,578 B1 | 5/2001 | Impraim et al. | |
| 6,228,580 B1 | 5/2001 | Blumenfeld et al. | |
| 6,232,462 B1 | 5/2001 | Collins et al. | |
| 6,268,128 B1 | 7/2001 | Collins et al. | |
| 6,277,579 B1 | 8/2001 | Lazar et al. | |
| 6,280,954 B1 | 8/2001 | Ulfendahl | |
| 6,326,136 B1 | 12/2001 | Lazar et al. | |
| 6,355,424 B1 | 3/2002 | Lorincz et al. | |
| 6,436,662 B1 | 8/2002 | Mielzynska et al. | |
| 6,521,190 B1 | 2/2003 | Edens et al. | |
| 6,544,732 B1 | 4/2003 | Chee et al. | |
| 6,583,278 B1 | 6/2003 | Carter | |
| 6,686,151 B1 | 2/2004 | Lazar et al. | |
| 6,828,098 B2 | 12/2004 | Langmore et al. | |
| 6,890,729 B2 | 5/2005 | Mielzynska et al. | |
| 6,969,585 B2 | 11/2005 | Lorincz et al. | |
| 6,977,148 B2 | 12/2005 | Dean et al. | |
| 7,001,776 B2 | 2/2006 | Botacini das Dores et al. | |
| 7,138,505 B1 | 11/2006 | Kuo et al. | |
| 7,371,518 B2 | 5/2008 | Lorincz et al. | |
| 7,439,016 B1 | 10/2008 | Anthony et al. | |
| 7,601,497 B2 | 10/2009 | Nazarenko et al. | |
| 7,812,144 B2 | 10/2010 | Karlsen | |
| 2001/0055766 A1 | 12/2001 | Aristarkhov et al. | |
| 2002/0012936 A1 | 1/2002 | Lorincz et al. | |
| 2002/0090635 A1 | 7/2002 | Xia et al. | |
| 2003/0096232 A1 | 5/2003 | Kris et al. | |
| 2003/0108897 A1 | 6/2003 | Drmanac | |
| 2003/0175765 A1 | 9/2003 | Kessler et al. | |
| 2003/0175789 A1 | 9/2003 | Weininger et al. | |
| 2004/0180362 A1 | 9/2004 | Lazar et al. | |
| 2004/0214302 A1 | 10/2004 | Anthony et al. | |
| 2005/0009063 A1 * | 1/2005 | Xia et al. | 435/6 |
| 2005/0032038 A1 | 2/2005 | Fisher et al. | |
| 2005/0032105 A1 | 2/2005 | Bair et al. | |
| 2005/0147996 A1 | 7/2005 | Sorge | |
| 2006/0051809 A1 | 3/2006 | Nazarenko et al. | |
| 2006/0160188 A1 | 7/2006 | Kurnit et al. | |
| 2006/0240449 A1 | 10/2006 | McGlennen et al. | |
| 2007/0154884 A1 | 7/2007 | Lorincz | |
| 2008/0200344 A1 | 8/2008 | Cheng | |
| 2008/0247914 A1 | 10/2008 | Edens et al. | |
| 2009/0032445 A1 | 2/2009 | Doak et al. | |
| 2009/0263819 A1 | 10/2009 | Muraca | |
| 2009/0286687 A1 | 11/2009 | Dressman et al. | |
| 2009/0298187 A1 | 12/2009 | Nazarenko et al. | |
| 2010/0081124 A1 | 4/2010 | Abravaya et al. | |
| 2010/0105060 A1 | 4/2010 | Eder et al. | |
| 2010/0126286 A1 | 5/2010 | Self et al. | |
| 2010/0129789 A1 | 5/2010 | Self et al. | |
| 2010/0159463 A1 | 6/2010 | Eder et al. | |
| 2010/0311039 A1 | 12/2010 | Lowe et al. | |
| 2011/0009277 A1 | 1/2011 | Devos et al. | |
| 2014/0087449 A1 | 3/2014 | Ballhause et al. | |

FOREIGN PATENT DOCUMENTS

| | | |
|---|---|---|
| EP | 0079139 | 5/1983 |
| EP | 0 163 220 | 12/1985 |
| EP | 0 167 366 | 1/1986 |
| EP | 0184017 | 6/1986 |
| EP | 0 281 927 | 9/1988 |
| EP | 0287961 A2 | 10/1988 |
| EP | 0 288 737 | 11/1988 |
| EP | 0333465 | 9/1989 |
| EP | 0 336 454 | 11/1992 |
| EP | 0540170 A1 | 5/1993 |
| EP | 0 144 914 | 6/1995 |
| EP | 0 703 296 | 3/1996 |
| EP | 1 806 410 A2 | 7/2007 |
| EP | 2 184 368 A1 | 5/2010 |
| JP | H07505759 A | 6/1995 |
| JP | H08505770 A | 6/1996 |
| JP | 2004-518421 A | 6/2004 |
| JP | 2009 106220 | 5/2009 |
| WO | 84/02721 | 7/1984 |
| WO | 8607387 | 12/1986 |
| WO | 88/03957 | 6/1988 |
| WO | 91/08312 | 6/1991 |
| WO | 93/10263 | 5/1993 |
| WO | 94/16108 | 7/1994 |
| WO | 94/16108 A1 | 7/1994 |
| WO | 95/16055 | 6/1995 |
| WO | 95/17430 | 6/1995 |
| WO | 96/40992 | 5/1996 |
| WO | 96/40992 | 12/1996 |
| WO | 97/05277 | 2/1997 |
| WO | 97/31256 | 8/1997 |
| WO | 98/18488 | 5/1998 |
| WO | 98/22620 | 5/1998 |
| WO | 98/59044 | 12/1998 |
| WO | 99/02488 | 1/1999 |
| WO | 99/29909 | 6/1999 |
| WO | 99/32654 | 7/1999 |
| WO | 99/36571 | 7/1999 |
| WO | 99/39001 | 8/1999 |

(56) References Cited

FOREIGN PATENT DOCUMENTS

| WO | 99/40224 | 8/1999 |
|---|---|---|
| WO | 99/50459 | 10/1999 |
| WO | 00/60116 | 10/2000 |
| WO | 01/36681 | 5/2001 |
| WO | 01/96608 A1 | 12/2001 |
| WO | 0196608 | 12/2001 |
| WO | 02066993 A1 | 8/2002 |
| WO | 2004/087950 | 10/2004 |
| WO | 2005/080602 | 9/2005 |
| WO | 2006039563 A2 | 4/2006 |
| WO | 2007/056723 | 5/2007 |
| WO | 2007/130519 A2 | 11/2007 |
| WO | 2008/036061 | 3/2008 |
| WO | 2008/139938 A1 | 11/2008 |
| WO | 2008149237 A2 | 12/2008 |
| WO | 2009/057993 A1 | 5/2009 |
| WO | 2009/123996 | 10/2009 |
| WO | 2010/004251 A1 | 1/2010 |
| WO | 2010/028382 | 3/2010 |
| WO | 2010/127228 A1 | 11/2010 |

OTHER PUBLICATIONS

International Search Report and Written Opinion of PCT/US2011/22887, dated Jun. 1, 2011.
International Preliminary Report on Patentability and Written Opinion of PCT/US2009/062061, dated May 12, 2011.
International Preliminary Report on Patentability and Written Opinion of PCT/US2009/062041, dated May 12, 2011.
GenBank Submission FJ429103. 2009 [Retrieved from the Internet May 20, 2011: www.ncbl.nlm.nih.gov/nuccore/FJ429103.1>]; in entirety.
Lowe et al.; "A Hybrid-Capture Assay to Detect HPV MRNA Ratios in Cervical Specimens"; Journal of Virological Methods; vol. 179; No. 1; Jan. 2012; pp. 142-147.
International Search Report Based on Application No. PCT/US2012/026380 Mailed Oct. 15, 2012.
Middleton, K. et al., "Organization of Human Papillomavirus Productive Cycle during Neoplastic Progression Provides a Basis for Selection of Diagnostic markers," Journal of Virology, Oct. 2003, pp. 10186-10201.
Stoler, M. et al., "Human Papillomavirus Type 16 and 18 Gene Expression in Cervical Neoplasias," Human Pathol. 23 (1992), pp. 117-128.
Higgins, G. et al., "Transcription patterns of human papillomavirus type 16 in genital intraepithelial neoplasia: evidence for promoter usage within the E7 open reading frame during epithelial differentiation," J. Gen. Virol. 73(1992), pp. 2047-2057.
Karlsen, F. et al., "Use of Multiple PCR Primer Sets for Optimal Detection of Human Papillomavirus," J. Clin. Microbiol. 34 (1996), pp. 2095-2100.
Park, JS et al., "Physical Status and Expression of HPV Genes in Cervical Cancers," Gynec. Oncol. 95 (1997), pp. 121-129.
Broker, TR, et al., "A Molecular Portrait of Human Papillomavirus Carcinogenesis," Cancer Cells 7 (1989), pp. 197-207.
Letter dated Jan. 6, 2010 to EPO re EP 1 038 022 (46 pages).
Letter to EPO dated Mar. 2, 209 re EP 1 038 022 (15 pages).
Letter to EPO dated Oct. 6, 2008 re EP 1 038 022 (27 pages).
Letter to EPO dated Aug. 8, 2008 re EP 1 038 022 (11 pages).
EPO decision dated May 27, 2008 re Opposition of EP 1 038 022 (19 pages).
Letter to EPO dated Jan. 25, 2008 re EP 1 038 022 (10 pages).
Letter to EPO dated Jan. 23, 2008 re EP 1 038 022 (6 pages).
Communication from EPO dated May 14, 2007 re EP 1 038 022 (8 pages).
Letter to EPO dated Oct. 4, 2006 re EP 1 038 022 (11 pages).
Letter to EPO dated Apr. 18, 2006 re EP 1 038 022 (10 pages).
Partial International Search Report for PCT/US2009/062041, mail date Jan. 5, 2010.
Partial International Search Report for PCT/US2009/062041, mail date Apr. 8, 2010.
Thai et al., "An HPV 16, 18, and 45 genotyping test based on Hybrid Capture technology," Journal of Clinical Virology 45, S1 (2009) pp. 593-597.
Kitagawa et al., "Comparison of Poly(A) Poly(dT) and Poly(I) Poly(dC) As Immunogens for the Induction of Antibodies to RNA-DNA Hybrids," Molecular Immunology, vol. 19, No. 3, pp. 413-420, 1982.
Ishikawa et al., "Enzyme-Labeling of Antiboldies and Their Fragments for Enzyme Immunoassay and Immunohistochemical Staining," Journal of Immunoassay and Immunochemistry, 4: 3, 209-327, 1983.
Means et al., "Chemical Modifications of Proteins: History and Applications," Bioconjugate Chem. 1990, 1, 2-12.
Jakobovits et al., "Analysis of homozygous mutant chimeric mice: Deletion of the immunoglobulin heavy-chain joining region blocks B-cell development and antibody production," Proc. Natl. Acad. Sci. USA, vol. 90, pp. 2551-2555, Mar. 1993 Genetics.
Jakobovits et al., "Germ-line transmission and expression of a human-derived yeast artificial chromosome," pp. 255-258, Nature, vol. 362, Mar. 18, 1993.
International Search Report for PCT/US2009/041033, dated Dec. 22, 2009.
Sigurdsson et al., "Human papillomavirus (HPV) in an icelandic population: the role of HPV DNA testing based on hybrid capture and PCR assays among women with screen-dtected abnormal PAP smears," In: International Journal of Cancer, Jul. 1997, vol. 72(3), pp. 446-452.
Michele De Villiers et al., "Classification of papillomarviruses," In: Virology, Jun. 2004, vol. 324(1), pp. 17-27—see table 3.
GenBank Accession No. K02718, "Human papillornavirus type 16 (HPV16), complete genome.", Mar. 18, 1994. See ncbi.nlm.nihgov/nuccore/333031.
GenBank Accession No. X74479, "human papiiiomavirus type 45 genomic DNA.", Apr. 18, 2005. See www.ncbi.nlm.nih.gov/nuccore/397022.
GenBank Accession No. X05015, "Human papillomavirus type 18 E6, E7, E1, E2, E4, E5, L1 & L2 genes.", Apr. 18, 2005. See http://www.ncbi.nlm.nih.gov/nuccore 60975.
GenBank Accession No. J04353, "Human papillomavirus type 31 (HPV-31), complete genome.", Mar. 18, 1994. See http://www.ncbi.nlm.nih.gov/nuccore/333048.
GenBank Accession No. M12732, "Human papillomavirus type 33, complete genome.", Mar. 21, 1994. See http://www.ncbi.nlm.nih.gov/nuccore/333049.
GenBank Accession No. M74117, "Human papillomavirus type 35, complete genome.", May 10, 2002 See http://www.ncbi.nlm.nih.gov/nuccore/333050.
GenBank Accession No. M62849, "Human papillomavirus ORFs.", Jan. 26, 2001. See http://www.ncbi.nlm.nih.gov/nuccore/333245.
GenBank Accession No. M62877, "Human papillomavirus type 51 genomic DNA, partial sequence.", Oct. 29, 1999. See http://www.ncbi.nlm.nih.gov/nuccore/333087.
GenBank Accession No. X74481, "Human papillomavirus type 52 genomic DNA.", Apr. 18, 2005. See http://www.ncbi.nlm.nih.gov/nuccore/397038.
GenBank Accession No. X74483, "Human papillomavirus type 56 genomic DNA.", Apr. 18, 2005. See http://www.ncbi.nlm.nih.gov/nuccore/397053.
GenBank Accession No. D90400, "Human papillomavirus type 58, complete genome.", Dec. 7, 2007. See http://www.ncbi.nlm.nih.gov/nuccore/222386.
GenBank Accession No. X77858, "Human papillomavirus type 59, complete viral genome.", Apr. 18, 2005. See http://www.ncbi.nlm.nih.gov/nuccore/557236.
GenBank Accession No. U31794, "Human papillomavirus type 66, complete genome.", Oct. 18, 1995. See http://www.ncbi.nlm.nih.gov/nuccore/1020290.
GenBank Accession No. X67161, "Human papillomavirus type L1 gene for major capsid protein.", Apr. 18, 2005. See http://www.ncbi.nlm.nih.gov/nuccore/1197494.
GenBank Accession No. AB027021, "Human papillomavirus type 82 DNA, complete genome.", Jun. 22, 2000. See http://www.ncbi.nlm.nih.gov/nuccore/6970427.

(56) References Cited

OTHER PUBLICATIONS

Kleter et al., "Development and clinical evaluation of a highly sensitive PCT-reverse hybridization line probe assay for detection and identification of anogenital human papillomavirus," In: Journal of clinical Micorbiology, Aug. 1999, vol. 37(8), pp. 2508-2517, see the whole document.
International Search Report and Written Opinion of PCT/US2010/048714, dated Dec. 10, 2010 (14 pages).
International Preliminary Report on Patentability and Written Opinion of PCT/US2009/041033, dated Oct. 19, 2010 (6 pages).
International Search Report and Written Opinion of PCT/US2010/047769, dated Nov. 9, 2010 (11 pages).
Pachowics, et al., "Sequence specific large volume sample prep solution utilizing Hybrid Capture technology," 41st Annual Oak Ridge Conference; Baltimore, MD; Apr. 16, 2009; retrieved from the Internet: http://www.aacc.org/events/meeting_proceeding/2009/Documents/OakRidge09AllPosters.pdf.
Keegan et al., "Comparison of HPV detection technologies: Hybrid capture 2, PreTect HPV-Proofer and analysis of HPV DNA viral load in HPV16, HPV18 and HPV33 E6/E7 mRNA positive specimens," Journal of Virological Methods, Jan. 1, 2009, pp. 61-66, vol. 155, No. 1, Elsevier BV, XP025799776.
Murphy et al., "Isolation of RNA from cell lines and cervical cytology specimens stored in BD SurePath (TM) preservative fluid and downstream detection of housekeeping gene and HPV E6 expression using real time RT-PCR," Journal of Virological Methods, Mar. 1, 2009, pp. 138-144, vol. 156, No. 1-2, Elsevier BV, XP025941323.
Powell et al., "Recovery of human papillomavirus nucleic acids from liquid-based cytology media," Journal of Virological Methods, Oct. 1, 2006, pp. 58-62, vol. 137, No. 1, Elsevier BV, XP005600251.
Nazarenko et al., "A novel method of HPV genotyping using Hybrid Capture sample preparation method combined with GP5+/6+ PCR and multiplex detection on Luminex XMAP," Journal of Virological Methods, Dec. 1, 2008, pp. 76-81, vol. 154, No. 1-2, Elsevier BV, XP025680302.
Taha et al., "Universal Collection Medium (UCM) is as suitable as the Standard Transport Medium (STM) for Hybrid Capture II (HC-2) assay," Journal of Virological Methods, May 1, 2006, pp. 32-35, vol. 36, No. 1, Elsevier BV, XP025178639.
Nindl et al., "Human Papillomavirus Distribution in Cervical Tissues of Different Morphology as Determined by Hybrid Capture Assay and PCR," International Journal of Gynecological Pathology, Jan. 1, 1997, pp. 197-204, vol. 16, No. 3, Lippincott-Raven Publishers, XP008011933.
Hernandez-Hernandez et al., "Association between high-risk human papillomavirus DNA load and precursor lesions of cervical cancer in Mexican women," Gynecologic Oncology, Aug. 2003, pp. 310-317, vol. 90, No. 2, Elsevier Science, XP002603500.
Tsai et al., "Association between Quantitative High-Risk Human Papillomavirus DNA Load and Cervical Intraepithelial Neoplasm Risk," Cancer Epidemiology, Biomarkers & Prevention: American Association for Cancer Research, Nov. 2005, pp. 2544-2549, vol. 14, No. 11 pt 1, XP002603501.
Moodley et al., "Human papillomavirus prevalence, viral load and pre-cancerous lesions of the cervix in women initiating highly active antiretroviral therapy in South Africa: a cross-sectional study," BMC Cancer, Aug. 7, 2009, pp. 1-8, vol. 9, No. 275, Biomed Central Ltd, XP002603502.
Ronco et al., "HPV triage for low grade (L-SIL) cytology is appropriate for women over 35 in mass cervical cancer screening using liquid based cytology," European Journal of Cancer, Feb. 1, 2007, pp. 476-480, vol. 43, No. 3, Pergamon Press, Oxford GB, XP005868775.
Clad et al.; "Performance of the Aptima High-Risk Human Papillomavirus MRNA Assay in a Referral Population in Comparison With Hybrid Capture 2 and Cytology"; Journal of Clinical Microbiology; Mar. 2011; LNKD-Pubmed:21191046; vol. 49; No. 3; Dec. 29, 2010; pp. 1071-1076; Abstract.
Li et al; Detection of Human Papillomavirus Genotypes With Liquid Bead Microarray in Cervical Lesions of Northern Chinese Patients; Cancer Genetics and Cytogenetics, Elsevier Science Publishing, New York, NY, US; vol. 182; No. 1; Mar. 6, 2008; pp. 12-17; Abstract.
Gheit et al.; "Development of a Sensitive and Specific Assay Combining Multiplex PCR and DNA Microarray Primer Extension to Detect High-Risk Mucosal Human Papillomavirus Types"; Journal of Clinical Microbiology, American Society for Microbiology, Washington, DC, US ; vol. 44; No. 6; Jun. 1, 2006; pp. 2025-2031; Abstract.
Han et al.; "Simultaneous Amplification and Identification of 25 Human Papillomavirus Types With Templex Technology"; Journal of Clinical Microbiology Nov. 2006 US LNKD-DOI:10.1128/JCM.01762-06; vol. 44; No. 11; Nov. 2006; pp. 4157-4162; Abstract.
Database EMBL [Online]; Jul. 19, 2007; "Sequence 25 From Patent EP1806410"; XP002675256; Retrieved From EBI Accession No. EMBL:CS642417; Database Accession No. CS642417; The Whole Document.
Database EMBL [Online]; Dec. 14, 2010; "Sequence 26 From U.S. Pat. No. 7,812,144"; XP00267527; Retrieved From EBI Accession No. EMBL:GX640151; Database Accession No. GX640151; The Whole Document.
Database Geneseq [Online]; Jan. 22, 2009; "HPV-16 E7/E6 Gene Target Sequence, Bases 752-774"; XP002675258, Retrieved From EBI Accesssion No. GSN:ATS82292; Database Accession No. ATS82292; The Whole Document.
Database Geneseq [Online]; Jan. 22, 2009; "HPV-16 E7/E6 Gene Target Sequence, Bases 698-720"; XP002675259 Retrieved From EBI Accession No. GSN:ATS82290; Database Accession No. ATS82290; The Whole Document.
Database Geneseq [Online]; Apr. 1, 2010; "HPV16 E7 Gene Forward RT-PCR Primer Seq ID 49"; XP002675260; Retrieved From EBI Accession No. GSN:AXU96631; Database Accession No. AXU96631; The Whole Document.
Database Geneseq [Online]; Apr. 21, 2005; "E7 Coding Region (1-87) Amplifying Sense PCR Primer, Seq ID No. 37"; XP002675261; Retrieved From EBI Accession No. GSN:ADX15568; Database Accession No. ADX15568; Sequence.
Yevgeniy S Belousov et al.: "Single nucleotide polymorphism genotyping by two colour melting curve analysis using the MGB elicpse TM probe system in challenging sequence environment" Human Genomics, Henry Stewart Publications, London, GB, vol. 1, No. 3, Jan. 1, 2004, pp. 209-217; XP001538494.
Gilbert et al., "The Isolation of Nucleic Acids from Fixed, Paraffin-Embedded Tissues—Which Methods are Useful When?", PLOS ONE, Jun. 6, 2007, vol. 2, No. 6, pp. 1-12.
Rivero et al., "Simple Salting-Out Method for DNA Extraction from Formalin-Fixed, paraffin-Embedded Tissues", Pathology Research and Practice, Jul. 10, 2006, vol. 202, No. 7, pp. 523-529.
International Search Report and Written Opinion of PCT/US2011/020107, dated Jul. 12, 2011.
Zientara et al., 1998 "Use of reverse transcriptase-polymerase chain reaction (RT-PCR) and dot-blot hybridization for the detection and identification of African horse sickness virus nucleic acids" Arch Virol 14:317-327.
Mansy et al., 1999 "A PCR Based DNA Hybridisation Capture System for the Detection of Human Cytomegalovirus. A Comparative Study with Other Identification Methods" Journal of Virological Methods 80:113-122.
Poulsen et al., 1999 "Detection of Clinical Vancomycin-Resistant Enterococci in Denmark by Multiplex PCR and Sandwich Hybridization" APMIS 107:404-12.
Sjoroos et al., 1998 "Time-Resolved Fluorometry Based Sandwich Hybridisation Assay for HLA-DQA1 Typing" Disease Markers 14:9-19.
Edman et al., 2000 "Pathogen Analysis and Genetic Predisposition Testing Using Microelectronic Arrays and Isothermal Amplification" Journal of Investigative Medicine, 48:93-101.
Monteiro et al.,1997 Evaluation of Performances of Three DNA Enzyme Immunoassays for Detection of Helicobacter pylori PCR Products from Biopsy Specimens Journal of Clinical Microbiology, 35;2931-2936.
Chiu et al., 1998 "Sandwich-type Deoxyribonucleic Acid Hybridization Assays Based on Enzyme Amplified Time-Resolved Fluorometry" Analyst , 123:1315-1319.

(56) References Cited

OTHER PUBLICATIONS

White et al., 1999 "Signal Amplification System for DNA Hybridization Assays Based on in vitro Expression of a DNA Label Encoding Apoaequorin" Nucleic Acids Research 27:i-viii.
Hakala et al., 1998 "Detection of Oligonucleotide Hybridization on a Single Microparticle by Time-Resolved Fluorometry: Quantitation and Optimization of a Sandwich Type Assay" Bioconjugate Chem. 9:316-321.
Zammatteo et al., 1997 "Comparison between Microwell and Bead Supports for the Detection of Human Cytomegalovirus Amplicons by Sandwich Hybridization" Analytical Biochemistry 253:180-189.
Fisher et al., 1997 "A System for the Quantitation of DNA Using a Microtiter Plate-Based Hybridization and Enzyme Amplification Technology" Analytical Biochemistry 251:280-287.
Wicks et al., 1998 "A Sandwich Hybridization Assay Employing Enzyme Amplification for Determination of Specific Ribosomal RNA from Unpurified Cell Lysates" Analytical Biochemistry 259:258-264.
Bruckner-Lea et al., 2000 "Rotating Rod Renewable Microcolumns for Automated, Solid-Phase DNA Hybridization Studies" Anal. Chem. 72:4135-4141.
Allen et al., 1998 "High Resolution Genetic Typing of the Class II HLA-DRB 1 Locus Using Group-Specific Amplification and SSO-Hybridisation in Microplates" Hereditas 129:161-167.
Alexandre et al., 1998 "Quantitative Determination of CMV DNA Using a Combination of Competitive PCR Amplification and Sandwich Hybridization" BioTechniques, 25: 676-683.
Hera et al., "Small Sample Whole-Genome Amplification," Optics East 2005, UCRL-PROC-216415, Lawrence Livermore National Laboratory, Oct. 21, 2005.
Brigotti, et al., "A rapid and sensitive method to measure the enzymatic activity of ribosome-inactivating proteins," Nucleic Acids Res., vol. 26, No. 18, pp. 4306-4307, 1998.
PCT/US2009/062061, International Searching Authority, Oct. 26, 2009 (6 pages).
PCT/US2009/062041, International Searching Authority, Oct. 26, 2009 (5 pages).
U.S. Appl. No. 12/622,131, titled "Multiple-Input Analytical System," filed Nov. 19, 2009 (not yet published).
Bhan et al., "2',5'-Linked oligo-3'-deoxyribonucleoside phosphorothioate chimeras: thermal stability and antisense inhibition of gene expression," Nucleic Acids Research, 1997, vol. 25, No. 16, pp. 3310-3317 (XP-002560367).
Genetech Diagnostics Pvt. Ltd., "Digene HBV Test Hybrid Capture II," Jun. 6, 2003 (XP-002560368).
Hantz et al., "Evaluation of accuracy of three assays for human papillomavirus detection and typing: Hybrid Capture 2, HPV Consensus kit and Amplicor HPV," Pathologie Biologie, Feb. 2008, vol. 56, No. 1, pp. 29-35 (XP002560369).
Sandri et al., "Comparison of the Digene HC2 Assay and the Roche Amplicor Human Papillomavirus (HPV) Test for Detection of High-Risk HPV Genotypes in Cervical Samples," Journal of Clinical Microbiology, Jun. 2006, vol. 44, No. 6, pp. 2141-2146 (XP002560370).
Boston Bioproducts Inc., "Protein Extraction buffers," Sep. 2, 2007 (XP002560371).
Bart "General Principles of Immunoprecipitation," Jul. 31, 2008 (XP002560372).
Broker et al., "A Molecular Portrait of Human Papillomavirus Carcinogenesis", Cancer Cells, vol. 7, pp. 197-208, 1989 (Roche EU Opposition).
Higgins et al., "Transcription Patterns of Human Papillomavirus Type 16 in Genital Intraepithelial Neoplasia: Evidence for Promoter Usage within the E7 Open Reading Frame during Epithelial Differentiation", Journal of General Virology, vol. 73, pp. 2047-2057, 1992 (Roche EU Opposition).
Karlsen et al., "Use of Multiple PCR Primer Sets for Optimal Detection of Human Papillomavirus", Journal of Clinical Microbiology, pp. 2095-2100, Sep. 1996 (Roche EU Opposition).

Park et al., "Physical Status and Expression of HPV Genes in Cervical Cancers", Gynecologic Oncology, vol. 65, pp. 121-129, 1997 (Roche EU Opposition).
Stoler et al., "Human Papillomavirus Type 16 and 18 Gene Expression in Cervical Neoplasias", Human Pathology, vol. 23, No. 2, pp. 117-128, Feb. 1992 (Roche EU Opposition).
De Villiers et al., "Classification of Papillomaviruses", Virology, vol. 324, pp. 17-27, 2004.
Howley et al., "A Rapid Method for Detecting and Mapping Homology between Heterologous DNAs", Journal of Biological Chemistry, vol. 254, No. 11, pp. 4879-4883, Jun. 10, 1979.
Law et al., "Conserved Polynucleotide Sequences Among the Genomics of Papillomaviruses", Journal of Virology, vol. 32, No. 1, pp. 199-207, Oct. 1979.
Heilman et al., "Cloning of Human Papilloma Virus Genomic DNAs and Analysis of Homologous Polynucleotide Sequences", Journal of Virology, vol. 36, No. 2, pp. 395-407, Nov. 1980.
Howard et al., "Optimizing the Hybrid Capture II Human Papillomavirus Test to Detect Cervical Intraepithelial Neoplasia", Obstetrics and Gynecology, vol. 100, No. 5, Part 1, pp. 972-980, Nov. 2002.
Lorincz, A.T., "Molecular Methods for the Detection of Human Papillomavirus Infection", Obstetrics and Gynecology Clinics of North America, vol. 23, No. 3, pp. 707-730, Sep. 1996.
Blair et al. "Herpes Simplex Virus Viron Stimulatory Protein mRNA Leader Contains Sequence Elements Which Increase Both Virus-Induced Transcription and tcRNA Stability," Journal of Virology, vol. 61, No. 8, pp. 2499-2508, Aug. 1987.
Chandler et al., Detection of Dengue-2 Viral RNA by Reversible Target Capture Flybridization., J. Clin. Microbiol., vol. 31 (10), pp. 2641-2647, 1993.
Mazzulli et al, 1999, Multicenter Comparison of the Digene Hybrid Capture CMV DNA Assay (version 2.0) the pp65 Antignenemia Assay, and Cell Culture for Detection of Cytomegalovirus Viremia, J Clin. Microbiol., vol. 37, No. 4, pp. 958-963, 1999.
Murakami et al., Fluorescent-Labeled Oligonucleotide Probes: Detection of Hybrid Formation in Solution by Fluorscence Polarization Spectroscopy, Nucleic Acids Res., vol. 19 (15), pp. 4097-4102, 1991.
Dunn and Hassell: "A Novel Method to Map Transcripts: Evidence for Homology between an Adenovirus niRNA and Discrete Multiple Regions of the Viral Genome" Cell, 12:23-36, Sep. 1977.
Coutlee et al., "Nonisotopic Detection of RNA in an Enzyme Imunoassay using a Monoclonal Antibody Against DNA-RNA Hybrids" Analytical Biochemistry 181:153-162, 1989.
Chen et al., "DNA Optical Sensor: A Rapid Method for the Detection of DNA Hybridization" Biosensors & Bioelectronics 13:451-458, 1998.
Chevrier et al., "Isolation of a Specific DNA fragment and Development of a PCR Based Method for the Detection of *Mycobacterium genavense*" FEMS Immunology and Medical Microbiology 23:243-452, 1999.
Hakala et al., "Simultaneous Detection of Several Oligonucleotides by Time-Resolved Fluorometry: The Use of a Mixture of Categorized Microparticles in a Sandwich Type Mixed-Phase Hybridization Assay" Nucleic Acid Research, 26:5581-5588, 1998.
Gelmetti et al., "Detection of Rabbit Haemorrhagic Disease Virus (RHDV) by In Situ Hybridisation With a Digoxigenin Labelled RNA Probe" Journal of Virological Methods 72:219-226, 1998.
Radtkey et al., "Rapid, High Fidelity Analysis of Simple Sequence Repeats on an Electronically Active DNA Microchip" Nucleic Acids Research 28:i-vi, 2000.
Namimatsu et al., "Detection of *Salmonella* by Using the Colorimetric DNA/rRNA Sandwich Hybridization in Microtiter Wells" J. Vet. Med. Sci. 62:615-619, 2000.
Lazar et al., 1999 "Hybrid Capture®: a Sensitive Signal Amplification-based Chemiluminescent Test for the Detection and Quantitation of Human Viral and Bacterial Pathogens".1. Clin. Ligand Assay 22:139-151.
Newman et al., 1989 "Solution Hybridization and Enzyme Immunoassay for Biotinylated DNA:RNA Hybrids to Detect Enteroviral RNA in Cell Culture" Mol. Cell Probes 3:375-382.

(56) References Cited

OTHER PUBLICATIONS

Lamoureux et al., 1997 "Detection of Campylobacter jejuni in Food and Poultry Viscera Using Immunomagnetic Separation and Microtitre Hybridization" J. Appl. Microbiol. 83:641-651.
Coutlee et al., 1990 "Quantitative Detection of Messenger RNA by Solution Hybridization and Enzyme Immunoassay" Biol. Chem. 265:11601-11604.
Stollar, B.D. and A. Rashtchian, 1987 "Immunochemical Approaches to Gene Probe Assays" Anal. Biochem. 161:387-394.
Blais, B.W., 1994 "Transcriptional Enhancement of the Listeria Monocytogenes PCR and Simple Immunoenzymatic Assay of the Product Using Anti-RNA:DNA Antibodies" Appl. Environ. Microbiol. 60:348-352.
Coutlee et al., 1991 "Detection of Transcripts of Human Papillomaviruses 16 and 18 in Cancer-derived Cell Lines and Cervical Biopsies by Enzyme Immunoassay for DNA-RNA Hybrids Following Solution Hybridization" J. Clin. Microbiol. 29:968-974.
Viscidi et al., 1989 "Monoclonal Antibody Solution Hybridization Assay for Detection of Human Immunodeficiency Virus Nucleic Acids" J. Clin. Microbiol. 27:120-125.
Boguslawski et al., 1986 "Characterization of Monoclonal Antibody to DNA:RNA and Its Application to immunodetection of Hybrids" J. Immunol. Methods 89:123-130.
Coutlee et al., 1989 "Immunodetection of DNA with Biotinylated RNA Probes: A Study of Reactivity of a Monoclonal Antibody to DNA-RNA Hybrids" Anal. Biochem. 181:96-105.
Coutlee et al., 1991 "Immunodetection of DNA with Biotinylated RNA Probes: A Study of Reactivity of a Monoclonal Antibody to DNA-RNA Hybrids" Anal. Biochem. 198:217 (Published erratum).
Coutlee et al., 1989 "Comparison of Calorimetric Fluorescent, and Enzymatic Amplification Substrate Systems in an Enzyme Immunoassay for Detection of DNA-RNA Hybrids" J. Clin. Microbiol. 27:1002-1007.
Dalrymple et al., DNA sequence of the herpes simplex virus type 1 gene whose product is responsible for transcriptional activation of immediate early promoters, Nucleic Acids Research, 1985, vol. 13, No. 21, pp. 7865-7879.
McLauchlan et al., DNA sequence homology between two co-linear loci on the HSV genome which have different transforming abilities, The EMBO Journal, 1983, vol. 2, No. 11, pp. 1953-1961.
Goldsborough et al., Nucleotide Sequence of Human Papillomavirus Type 31: A Cervical Neoplasia Associated Virus, Virology, 1989, vol. 171, pp. 306-311.
McGeoch et al., "DNA Sequence and Genetic Content of the Hindlll 1 Region in the Short Unique Component of the Herpes Simplex Virus Type 2 Genome; Identification of the Gene Encoding Glycoprotein G, and Evolutionary Comparisons," J. Gen. Virol., 1987, vol. 68, pp. 19-38.
McGeoch et al., The Complete DNA Sequence of the Long Unique Region in the Genome of Herpes Simplex Virus Type I, 1 Gen Virol., 1988, vol. 69, pp. 1531-1574.
Yamada et al., Human Papillomavirus Type 16 Variant Lineages in United States Populations Characterized by Nucleotide Sequence Analysis of the E6, L2, and LI Coding Segments, J. Virol., Dec. 1995, vol. 69, No. 12, pp. 7743-7753.
Swain et al., Nucleotide Sequence of the Herpes Simplex Virus Type 2 Thymidine Kinase Gene, Virol., Jun. 1983, vol. 46, No. 3, pp. 1045-1050.
Delius et al., Primer-Directed Sequencing of Human Papillomavirus Types, Current Topics in Microbiology and Immunology, 1994, vol. 185, pp. 13-31.
Blair et al., Herpes Simplex Virus Virion Stimulatory Protein mRNA Leader Contains Sequence Elements Which Increase Both Virus-Induced Transcription and mRNA Stability, J. Virol., Aug. 1987, vol. 62, No. 2, pp. 444-453.
Larder et al., Related functional domains in virus DNA polymerases, The EMBO J., 1987, vol. 6, No. 1, pp. 169-175.
McGeoch et al., Structures of Herpes Simplex Virus Type 1 Genes Required Replication of Virus DNA, J. Virol., vol. 62, No. 2, pp. 444-453, 1988.
Lowe et al., "HPV Genotype Detection Using Hybrid Capture Sample Preparation Combined with Whole Genome Amplification and Multiplex Detection with Luminex XMAP," Journal of Molecular Diagnostics; Nov. 6, 2010; pp. 847-853; vol. 12; No. 6; American Society for Investigative Pathology.
Partial European Search Report of EP10185824; mailed Feb. 16, 2011 (8 pages).
Scott et al., "Detection of herpes simplex virus type 1 shedding in the oral cavity by polymerase chain reaction and enzyme-linked immunosorbent assay at the prodromal stage of recrudescent herpes labialis," Journal of Oral Pathology & Medicine; Aug. 1997; pp. 305-309; vol. 26; No. 7; XP009143938.
Ryncarz et al., "Development of a High-Throughput Quantitative Assay for Detecting Herpes Simplex Virus DNA in Clinical Samples," Journal of Clinical Microbiology; Jun. 1999; pp. 1941-1947; vol. 37, No. 6; American Society for Microbiology.
Chinese First Action dated Apr. 26, 2013, issued in Application No. 201180012414.0 and English translation thereof.
Chinese Office Action (Second) issued in Application No. 200980143682.9, dated Aug. 5, 2013, and English translation thereof.
Instructions RIPA Buffer (No. 89900 89901) [online] Thermo Scientific, 2006, [<Retrieved from the Internet: piercenet.com/instructions/2161782.pdf>].
Japanese Notice of Reasons for Rejection dated Nov. 27, 2013, issued in Application No. 2011-533405 and English translation thereof.
Notice of Reasons for Rejection dated Aug. 26, 2013, issued in Japanese Application No. 2011-505244 and English translation thereof.
International Preliminary Report on Patentability dated Aug. 27, 2013, issued in Application No. PCT/US2012/026380.
Chinese First Action dated Aug. 2, 2013, issued in Application No. 201180016276.3 and English translation thereof.
Molijin A. et al., "Molecular diagnosis of human papillomavirus (HPV) infections," Journal of Clinical Virology, 2005, Vo. 32S at pp. S43-S51.
Chinese First Action dated Apr. 15, 2013, issued in Application No. 201080018737.6.
European Office Action dated Oct. 18, 2013, issued in Application No. 11 726 003.4-1403.
Rych et al., A computer program for choosing optimal oligonucleotides for filter hybridization, sequence and in vitro amplification of DNA. Nucleic Acids Research, 17, 8543-8551, 1989.
Luo et al., "Adiponectin stimulates human osteoblasts proliferation and differentiation via the MAPK signaling pathway," Experimental Cell Research, Academic Press, US, 309:1, (Sep. 10, 2005) 99-109, XP005037411.
Ouitas N. et al., "A Novel ex vivo skin model for the assessment of the potential transcutaneous anti-inflammatory effect of topically applied Harpagophytum procumbens extract," International Journal of Pharmaceutics, Elsevier BV, NL, 376: 1-2, (Jul. 6, 2009), 63-68, XP026185227.
Scholz et al., "Analysis of human immunodeficieny virus matrix domain replacements," Virology, Elsevier, Amsterdam, NL. 371: 2, (Nov. 8, 2007) 322-335, XP022439785.
Xie H. et al., "Apelin in and its receptor are expressed in human obsteoblasts," Regulatory Peptides, Elsevier Science B.V., NL, 134: 2-3, (May 15, 2006), 118-125, XP27895144.
Zhang W. et al., "Bone-Targeted Overespression of Bcl-2 Increases Osteoblast Adhesion and Differentiation and Inhibits of Mineralization In Vitro," Calcified Tissue International, Springer-Verlag, NE, 80: 2, (Feb. 2, 2007), 111-122.
European Office Action dated Jul. 14, 2014, issued in Application No. 10 755 291.1-1406.
Takaaki Tamura, "Analysis of Genome DNA, Genetic Engineering Testing Notebook." (Idenshi-Kogaku Jikken Notebook), May 15, 2006, Revised Second Edition, p. 99-100.
General Catalog of Reagemts, Funakoshi, Part II, Best Selection, 2004, p. 518.
Japanese Notice of Reasons for Rejection dated Dec. 17, 2014, issued in Application No. 2012-528961 and English translation thereof.
Supplementary European Search Report of PCT/US2006/060603, dated Jul. 7, 2010 (8 pages).

(56) References Cited

OTHER PUBLICATIONS

Lowe, et al., "A computer program for selection of oligonucleotide primers for polymerase chain reactions", Nucleic Acid Res., vol. 18, No. 7, pp. 1757-1761 (1990).

International Search Report and Written Opinion of PCT/US2010/022264 dated Jun. 7, 2010 (19 pages).

Cohenford et al., "C-195. Rapid Detection of Chlamydia trachomatis from Specimens Collected from the ThinPrep Pap Test using Molecular Beacons and the Roche LightCycler," Abstracts of the General Meeting of the American Society for Microbiology, The Society, Washington, DC. (Jan. 1, 2001), p. 195, vol. 101, XP001098006.

Gentech Diagnostics: "Chlamydia DNA Test Kit," (Jun. 6, 2008), XP002578832, Retrieved from the Internet: URL: http://www.gentechin.com/chlamydiatestkit.htm.

Taha et al., "Universal Collection Medium (UCM) is as suitable as the Standard Transport Medium (STM) for Hybrid Capture II (HC-2) assay," Journal of Clinical Virology, (May 1, 2006), pp. 32-35, vol. 36, No. 1, XP005367693.

Darwin et al., "Comparison of Digene Hybrid Capture 2 and Conventional Culture for Detection of Chlamydia trachomatis and Neisseria gonorrhoeae in Cervical Specimens," Journal of Clinical Microbiology, (Feb. 2002), pp. 641-644, vol. 40, No. 2, XP002578833.

Nazarenko et al., "A novel method of HPV genotyping using Hybrid Capture sample preparation method combined with GP5+/6+ PCR and multiplex detection on Luminex XMAP," Journal of Clinical Virology, (Dec. 1, 2008), pp. 76-81, vol. 154, No. 1-2, XP025680302.

International Search Report and Written Opinion of PCT/US10/33146, dated Aug. 5, 2010 (9 pages).

A Lorincz, "Hybrid Capture," Clin. Chem., (Jun. 1998), pp. 1363, vol. 44, No. 6.

Vernick et al., "The HPV DNA virus hybrid capture assay: What is it- and where do we go from here?" MLO Med. Lab. Obs., (Mar. 2003), pp. 8-10, 13, vol. 35, No. 3.

* cited by examiner

COMPOSITIONS AND METHODS FOR RECOVERY OF NUCLEIC ACIDS OR PROTEINS FROM TISSUE SAMPLES FIXED IN CYTOLOGY MEDIA

CROSS REFERENCE TO RELATED APPLICATIONS

This application claims priority from U.S. Provisional Patent Application Ser. No. 61/242,258 (filed Sep. 14, 2009) and U.S. Provisional Patent Application Ser. No. 61/253,300 (filed Oct. 20, 2009), the contents of which are incorporated herein by reference in their entireties. A PCT application entitled "Compositions And Methods For Recovery Of Nucleic Acids Or Proteins From Tissue Samples Fixed In Cytology Media" (filed concurrently herewith on Sep. 14, 2010) is also incorporated herein by reference in its entirety.

FIELD OF THE INVENTION

Compositions, methods, and kits for improved recovery of nucleic acids or proteins from fixed biological samples are described.

BACKGROUND OF THE INVENTION

In the fields of histology, pathology, and cell biology, fixation is a chemical process by which biological samples are preserved from decay. Fixation terminates any ongoing biochemical reactions, and may also increase the mechanical strength or stability of the treated samples. The purpose of fixation is to preserve a sample of biological material as close to its natural state as possible. Fixed samples are used for examination or analysis.

Fixatives can be classified as cross-linking or precipitating fixatives.

Cross-linking fixatives act by creating covalent chemical bonds between proteins in tissue. This anchors soluble proteins to the cytoskeleton, and lends additional rigidity to the tissue. Aldehydes are by far the most commonly used cross-linking fixatives. Although aldehyde-fixed biological samples are useful for histological, pathological, and cell biological applications, they pose several problems for molecular analysis of the preserved sample. For example, fixation with aldehydes causes protein-protein, DNA-protein, and RNA-protein cross-links to form, which interferes with the ability to extract and purify proteins and nucleic acids. Moreover, reversal of cross-linking often results in free aldehyde in the sample, which can interfere with functional proteins (such as enzymes or antibodies), nucleic acid probes, resins, or any other functional reagents with amino groups that are used in sample processing and analysis.

As such, there remains a need for methods and compositions that increase the efficiency of isolating various components (such as nucleic acids, proteins, and organelles) from biological samples fixed in fixed in aldehyde-based cytology media.

Precipitating fixatives act by reducing the solubility of protein molecules and disrupting hydrophobic interactions. As this process is very different from cross-linking fixation, biological samples fixed with precipitating fixatives often must be processed with different reagents and methods than those used with cross-linking fixatives. Alcohols are commonly used precipitating fixatives. There is a need for methods and compositions that increase the efficiency of isolating various components (such as nucleic acids, proteins, and organelles) from biological samples fixed in alcohol-based cytology media.

Therefore, there remains is a need for methods and reagents that are useful in extracting various components from fixed biological samples (such as nucleic acids, proteins, and organelles), regardless of the type fixative used. In particular, lysis solutions are needed that may be used for biological samples fixed in cytology media that is cross-linking-based, precipitating-based, or both.

SUMMARY OF THE INVENTION

The present disclosure provides a lysis composition that can be used to lyse biological samples fixed in cytology media. The cytology medium can comprise either precipitating or cross-linking fixatives, or both.

The present disclosure also provides methods of preparing a fixed biological sample for analysis comprising lysing the fixed biological sample in the presence of a buffered composition. The lysing process creates a lysate, from which a component can be isolated. The isolated component can be subjected to analysis.

The methods and compositions disclosed herein exhibit improved extraction of biological samples regardless of the fixative used in the cytology medium.

DETAILED DESCRIPTION OF THE INVENTION

Figure 1A:
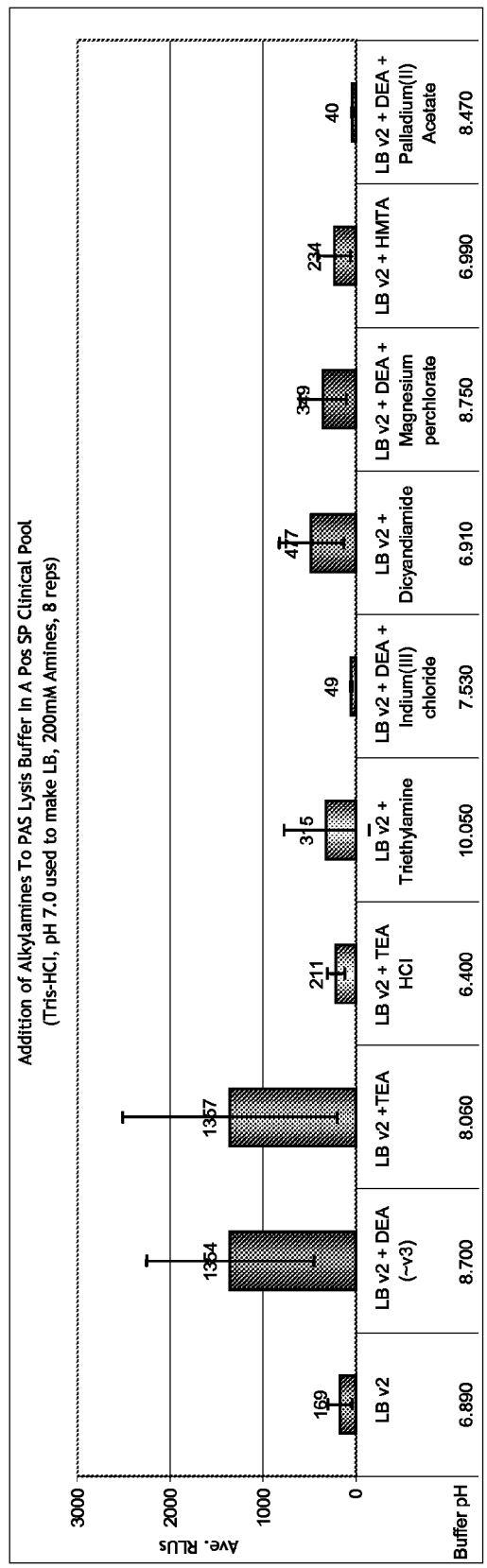
FIGS. 1A and 1B show the effects of various amine-containing compounds on the extraction of DNA from aldehyde-fixed clinical cervical samples using a lysis solution comprising 150 mM Tris. Columns represent average relative light unit (RLU), with error bars representing the standard deviation of the eight replicates tested. The pH of each lysis solution is also displayed. Abbreviations: LB v2=lysis solution of: (1) 3% (v/v) Brij-58, and (2) 150 mM Tris-HCl; DEA=diethanolamine; TEA=triethanolamine; TEA HCl=triethanolamine hydrogen chloride; HMTA=hexamethylene-tetramine; EA=ethanolamine; EDA=ethylenediamine; DETA=diethylenetriamine; DEA HCl=diethanolamine hydrogen chloride. Typically, 1.5 mL of sample is added to 1 mL of lysis buffer, plus 25 µl of Proteinase K (10 mg/ml stock) and 60 µl of 1.5% (v/v) AxpH™ DNA-affinity magnetic beads.

The present disclosure relates to reagents and methods that are useful in universal protocols for extracting various components from biological samples fixed in a variety of fixative materials and amenable to high through-put automation.

In particular, the present disclosure provides a composition comprising a fixed biological sample and a lysis solution, the lysis solution comprising at least two amines.

As used herein, the term "fixed biological sample" refers to any biological material that has been preserved with a fixative agent, including but not limited to paraffin-embedded tissues or organs, tissue samples stored in liquid cryological preservation media, and cervical or gynecological swabs stored in liquid cryological preservation material. The fixative agent may be a cross-linking fixative agent or a precipitating fixative agent. Cross-linking fixatives include without limitation aldehydes (such as formaldehyde, paraformaldehyde, and glutaraldehyde), osmium tetroxide, potassium dichromate, chromic acid, and potassium permanganate. Precipitating fixative solutions include without limitation alcohols (such as ethanol and methanol) and acetic acid.

An example of an alcohol-based cytology medium is PRESERVCYT™. An example of an aldehyde-based cytology medium is SUREPATH™.

As used herein, the terms "lysis" and "lysing" refer to the act of disrupting the integrity of a cell wall; a cell membrane; or an organelle defined by a lipid membrane, including but not limited to endoplasmic reticulum, Golgi apparatus, lysosome, mitochondrion, nucleus, vacuole, and vesicle. Exemplary methods of lysis include mechanical lysis, such as by sonication or cytolysis; and chemical lysis, including use of detergents such as polyoxyethylene (20) cetyl ether (sold commercially as Brij-58), 3-[(3-cholamidopropyl)dimethylammonio]-1-propanesulfonate (sold commercially as CHAPS), NONIDET™ P-40 (also known as Igepal CA-630, tert-octylphenoxy poly(oxyethylene)ethanol), deoxycholate, TritonTRITON™ X-100 (also known as 4-(1,1,3,3-Tetramethylbutyl)phenyl-polyethylene glycol), sodium dodecyl sulfate (sold commercially as SDS), and/or polysorbate surfactants (sold commercially as TWEEN).

As used herein, "lysis solution" refers to any solution that is useful for lysing a cell. Exemplary lysis solutions include without limitation hypotonic lysis solutions and detergent-based lysis solutions, including but not limited to lysis solutions comprising polyoxyethylene (20) cetyl ether (sold commercially as Brij-58), 3-[(3-cholamidopropyl)dimethylammonio]-1-propanesulfonate (sold commercially as CHAPS), NONIDET P-40 (also known as Igepal CA-630, tert-octylphenoxy poly(oxyethylene)ethanol), deoxycholate, TRITON X-100 (also known as 4-(1,1,3,3-Tetramethylbutyl)phenyl-polyethylene glycol), sodium dodecyl sulfate (sold commercially as SDS), and/or polysorbate surfactants (sold commercially as TWEEN). The precise type and formulation of the lysis solution can be readily determined by a person having ordinary skill in the art according to the sample type, the method of lysis, the analyte of interest, and the method of analysis to be used.

Amines are derivatives of ammonia and are classified according to the number of hydrogens of ammonia replaced by organic groups. Primary amines are compounds having the formula of $(RNH_2)$ wherein R is an organic group. Secondary amines are compounds having the formula of $(R_2NH)$ wherein R is an organic group. Tertiary amines are compounds having the formula of $(R_3N)$, wherein R is an organic group. Secondary and tertiary amines may also be cyclic molecules in which the nitrogen atom of the amine group is integral to the ring structure. Examples of amines include methylamine, dimethylamine, diethylamine, hydroxylamine (HA), trimethylamine, triethylamine, monoethanolamine (EA), diethanolamine (DEA), triethanolamine (TEA), tris (hydroxymethyl)aminomethane (TRIS), ethylenediamine, diethylenetriamine (DETA) or hexamethylenetetramine (HMTA), aniline, and amino acids. Other examples of amines will be readily apparent to a person having ordinary skill in the art. Any amine may used in the compositions and methods disclosed herein.

In one embodiment, the amount of each amine in the lysis solution is selected from the group consisting of: about 25 mM or greater, about 50 mM or greater, about 100 mM or greater, about 150 mM or greater, about 200 mM or greater, 250 mM or greater, about 260 mM or greater, about 270 mM or greater, about 280 mM or greater, about 290 mM or greater, about 300 mM or greater, about 310 mM or greater, about 320 mM or greater, about 330 mM or greater, about 340 mM or greater, about 350 mM or greater, about 400 mM or greater, about 450 mM or greater, about 500 mM or greater, from about 25 mM to about 100 mM, from about 25 mM to about 150 mM, from about 25 mM to about 200 mM, from about 25 mM to about 250 mM, from about 25 mM to about 260 mM, from about 25 mM to about 270 mM, from about 25 mM to about 280 mM, from about 25 mM to about 290 mM, from about 25 mM to about 300 mM, from about 25 mM to about 310 mM, from about 25 mM to about 320 mM, from about 25 mM to about 330 mM, from about 25 mM to about 340 mM, from about 25 mM to about 350 mM, from about 25 mM to about 400 mM, from about 25 mM to about 450 mM, from about 25 mM to about 500 mM, from about 50 mM to about 100 mM, from about 50 mM to about 150 mM, from about 50 mM to about 200 mM, from about 50 mM to about 250 mM, from about 50 mM to about 260 mM, from about 50 mM to about 270 mM, from about 50 mM to about 280 mM, from about 50 mM to about 290 mM, from about 50 mM to about 300 mM, from about 50 mM to about 310 mM, from about 50 mM to about 320 mM, from about 50 mM to about 330 mM, from about 50 mM to about 340 mM, from about 50 mM to about 350 mM, from about 50 mM to about 400 mM, from about 50 mM to about 450 mM, from about 50 mM to about 500 mM, from about 100 mM to about 150 mM, from about 100 mM to about 200 mM, from about 100 mM to about 250 mM, from about 100 mM to about 260 mM, from about 100 mM to about 270 mM, from about 100 mM to about 280 mM, from about 100 mM to about 290 mM, from about 100 mM to about 300 mM, from about 100 mM to about 310 mM, from about 100 mM to about 320 mM, from about 100 mM to about 330 mM, from about 100 mM to about 340 mM, from about 100 mM to about 350 mM, from about 100 mM to about 400 mM, from about 100 mM to about 450 mM, from about 100 mM to about 500 mM, from about 150 mM to about 200 mM, from about 150 mM to about 250 mM, from about 150 mM to about 260 mM, from about 150 mM to about 270 mM, from about 150 mM to about 280 mM, from about 150 mM to about 290 mM, from about 150 mM to about 300 mM, from about 150 mM to about 310 mM, from about 150 mM to about 320 mM, from about 150 mM to about 330 mM, from about 150 mM to about 340 mM, from about 150 mM to about 350 mM, from about 150 mM to about 400 mM, from about 150 mM to about 450 mM, from about 150 mM to about 500 mM, from about 200 mM to about 250 mM, from about 200 mM to about 260 mM, from about 200 mM to about 270 mM, from about 200 mM to about 280 mM, from about 200 mM to about 290 mM, from about 200 mM to about 300 mM, from about 200 mM to about 310 mM, from about 200 mM to about 320 mM, from about 200 mM to about 330 mM, from about 200 mM to about 340 mM, from about 200 mM to about 350 mM, from about 200 mM to about 400 mM, from about 200 mM to about 450 mM, from about 200 mM to about 500 mM, from about 250 mM to about 260 mM, from about 250 mM to about 270 mM, from about 250 mM to about 280 mM, from about 250 mM to about 290 mM, from about 250 mM to about 300 mM, from about 250 mM to about 310 mM, from about 250 mM to about 320 mM, from about 250 mM to about 330 mM, from about 250 mM to about 340 mM, from about 250 mM to about 350 mM, from about 250 mM to about 400 mM, from about 250 mM to about 450 mM, from about 250 mM to about 500 mM, from about 260 mM to about 270 mM, from about 260 mM to about 280 mM, from about 260 mM to about 290 mM, from about 260 mM to about 300 mM, from about 260 mM to about 310 mM, from about 260 mM to about 320 mM, from about 260 mM to about 330 mM, from about 260 mM to about 340 mM, from about 260 mM to about 350 mM, from about 260 mM to about 400 mM, from about 260 mM to about 450 mM, from about 260 mM to about 500 mM, from about 270 mM to about 280 mM, from about 270 mM to about 290 mM, from about 270 mM to about 300 mM, from about 270 mM to about 310 mM, from about 270 mM to about 320 mM, from about 270 mM to about 330 mM, from about 270 mM to about 340 mM, from about 270 mM to about 350 mM, from about 270 mM to about 400 mM, from about 270 mM to about 450 mM, from about 270 mM to about 500 mM, from about 280 mM to about 290 mM, from about 280 mM to about 300 mM, from about 280 mM to about 310 mM, from about 280 mM to about 320 mM, from about 280 mM to about 330 mM, from about 280 mM to about 340 mM, from about 280 mM to about 350 mM, from about 280 mM to about 400 mM, from about 280 mM to about 450 mM, from about 280 mM to about 500 mM, from about 290 mM to about 300 mM, from about 290 mM to about 310 mM, from about 290 mM to about 320 mM, from about 290 mM to about 330 mM, from about 290 mM to about 340 mM, from about 290 mM to about 350 mM, from about 290 mM to about 400 mM, from about 290 mM to about 450 mM, from about 290 mM to about 500 mM, from about 300 mM to about 310 mM, from about 300 mM to about 320 mM, from about 300 mM to about 330 mM, from about 300 mM to about 340 mM, from about 300 mM to about 350 mM, from about 300 mM to about 400 mM, from about 300 mM to about 450 mM, from about 300 mM to about 500 mM, from about 310 mM to about 320 mM, from about 310 mM to about 330 mM, from about 310 mM to about 340 mM, from about 310 mM to about 350 mM, from about 310 mM to about 400 mM, from about 310 mM to about 450 mM, from about 310 mM to about 500 mM, from about 320 mM to about 330 mM, from about 320 mM to about 340 mM, from about 320 mM to about 350 mM, from about 320 mM to about 400 mM, from about 320 mM to about 450 mM, from about 320 mM to about 500 mM,), from about 330 mM to about 340 mM, from about 330 mM to about 350 mM, from about 330 mM to about 400 mM, from about 330 mM to about 450 mM, from about 330 mM to about 500 mM, from about 340 mM to about 350 mM, from about 340 mM to about 400 mM, from about 340 mM to about 450 mM, from about 340 mM to about 500 mM, from about 350 mM to about 400 mM, from about 350 mM to about 450 mM, from about 350 mM to about 500 mM, from about 400 mM to about 450 mM, from about 400 mM to about 500 mM, from about 450 mM to about 500 mM, about 100 mM, or about 150 mM, or about 200 mM, or about 250 mM, or about 260 mM, or about 270 mM, or about 280 mM, or about 290 mM, or about 300 mM, or about 310 mM, or about 320 mM, or about 330 mM, or about 340 mM, or about 350 mM, or about 400 mM, or about 450 mM, or about 500 mM.

In one embodiment, the amount of each amine in the lysis solution is selected from the group consisting of: from about 0.1% (w/v) to about 0.2% (w/v), from about 0.1% (w/v) to about 0.3% (w/v), from about 0.1% (w/v) to about 0.4% (w/v), from about 0.1% (w/v) to about 0.5% (w/v), from about 0.1% (w/v) to about 0.6% (w/v), from about 0.1% (w/v) to about 0.7% (w/v), from about 0.1% (w/v) to about 0.8% (w/v), from about 0.1% (w/v) to about 0.9% (w/v), from about 0.1% (w/v) to about 1.0% (w/v), from about 0.1% (w/v) to about 1.5% (w/v), from about 0.1% (w/v) to about 2.0% (w/v), from about 0.1% (w/v) to about 2.5% (w/v), from about 0.1% (w/v) to about 3% (w/v), from about 0.1% (w/v) to about 4% (w/v), from about 0.1% (w/v) to about 5% (w/v), from about 0.1% (w/v) to about 7% (w/v), from about 0.1% (w/v) to about 9% (w/v), from about 0.1% (w/v) to about 11% (w/v), from about 0.1% (w/v) to about 13% (w/v), from about 0.1% (w/v) to about 15% (w/v), from about 0.2% (w/v) to about 0.3% (w/v), from about 0.2% (w/v) to about 0.4% (w/v), from about 0.2% (w/v) to about 0.5% (w/v), from about 0.2% (w/v) to about 0.6% (w/v), from about 0.2% (w/v) to about 0.7% (w/v), from about 0.2% (w/v) to about 0.8%

(w/v), from about 0.2% (w/v) to about 0.9% (w/v), from about 0.2% (w/v) to about 1.0% (w/v), from about 0.2% (w/v) to about 1.5% (w/v), from about 0.2% (w/v) to about 2.0% (w/v), from about 0.2% (w/v) to about 2.5% (w/v), from about 0.2% (w/v) to about 3% (w/v), from about 0.2% (w/v) to about 4% (w/v), from about 0.2% (w/v) to about 5% (w/v), from about 0.2% (w/v) to about 7% (w/v), from about 0.2% (w/v) to about 9% (w/v), from about 0.2% (w/v) to about 11% (w/v), from about 0.2% (w/v) to about 13% (w/v), from about 0.2% (w/v) to about 15% (w/v), from about 0.3% (w/v) to about 0.4% (w/v), from about 0.3% (w/v) to about 0.5% (w/v), from about 0.3% (w/v) to about 0.6% (w/v), from about 0.3% (w/v) to about 0.7% (w/v), from about 0.3% (w/v) to about 0.8% (w/v), from about 0.3% (w/v) to about 0.9% (w/v), from about 0.3% (w/v) to about 1.0% (w/v), from about 0.3% (w/v) to about 1.5% (w/v), from about 0.3% (w/v) to about 2.0% (w/v), from about 0.3% (w/v) to about 2.5% (w/v), from about 0.3% (w/v) to about 3% (w/v), from about 0.3% (w/v) to about 4% (w/v), from about 0.3% (w/v) to about 5% (w/v), from about 0.3% (w/v) to about 7% (w/v), from about 0.3% (w/v) to about 9% (w/v), from about 0.3% (w/v) to about 11% (w/v), from about 0.3% (w/v) to about 13% (w/v), from about 0.3% (w/v) to about 15% (w/v), from about 0.4% (w/v) to about 0.5% (w/v), from about 0.4% (w/v) to about 0.6% (w/v), from about 0.4% (w/v) to about 0.7% (w/v), from about 0.4% (w/v) to about 0.8% (w/v), from about 0.4% (w/v) to about 0.9% (w/v), from about 0.4% (w/v) to about 1.0% (w/v), from about 0.4% (w/v) to about 1.5% (w/v), from about 0.4% (w/v) to about 2.0% (w/v), from about 0.4% (w/v) to about 2.5% (w/v), from about 0.4% (w/v) to about 3% (w/v), from about 0.4% (w/v) to about 4% (w/v), from about 0.4% (w/v) to about 5% (w/v), from about 0.4% (w/v) to about 7% (w/v), from about 0.4% (w/v) to about 9% (w/v), from about 0.4% (w/v) to about 11% (w/v), from about 0.4% (w/v) to about 13% (w/v), from about 0.4% (w/v) to about 15% (w/v), from about 0.5% (w/v) to about 0.6% (w/v), from about 0.5% (w/v) to about 0.7% (w/v), from about 0.5% (w/v) to about 0.8% (w/v), from about 0.5% (w/v) to about 0.9% (w/v), from about 0.5% (w/v) to about 1.0% (w/v), from about 0.5% (w/v) to about 1.5% (w/v), from about 0.5% (w/v) to about 2.0% (w/v), from about 0.5% (w/v) to about 2.5% (w/v), from about 0.5% (w/v) to about 3% (w/v), from about 0.5% (w/v) to about 4% (w/v), from about 0.5% (w/v) to about 5% (w/v), from about 0.5% (w/v) to about 7% (w/v), from about 0.5% (w/v) to about 9% (w/v), from about 0.5% (w/v) to about 11% (w/v), from about 0.5% (w/v) to about 13% (w/v), from about 0.5% (w/v) to about 15% (w/v), from about 0.6% (w/v) to about 0.7% (w/v), from about 0.6% (w/v) to about 0.8% (w/v), from about 0.6% (w/v) to about 0.9% (w/v), from about 0.6% (w/v) to about 1.0% (w/v), from about 0.6% (w/v) to about 1.5% (w/v), from about 0.6% (w/v) to about 2.0% (w/v), from about 0.6% (w/v) to about 2.5% (w/v), from about 0.6% (w/v) to about 3% (w/v), from about 0.6% (w/v) to about 4% (w/v), from about 0.6% (w/v) to about 5% (w/v), from about 0.6% (w/v) to about 7% (w/v), from about 0.6% (w/v) to about 9% (w/v), from about 0.6% (w/v) to about 11% (w/v), from about 0.6% (w/v) to about 13% (w/v), from about 0.6% (w/v) to about 15% (w/v), from about 0.7% (w/v) to about 0.8% (w/v), from about 0.7% (w/v) to about 0.9% (w/v), from about 0.7% (w/v) to about 1.0% (w/v), from about 0.7% (w/v) to about 1.5% (w/v), from about 0.7% (w/v) to about 2.0% (w/v), from about 0.7% (w/v) to about 2.5% (w/v), from about 0.7% (w/v) to about 3% (w/v), from about 0.7% (w/v) to about 4% (w/v), from about 0.7% (w/v) to about 5% (w/v), from about 0.7% (w/v) to about 7% (w/v), from about 0.7% (w/v) to about 9% (w/v), from about 0.7% (w/v) to about 11% (w/v), from about 0.7% (w/v) to about 13% (w/v), from about 0.7% (w/v) to about 15% (w/v), from about 0.8% (w/v) to about 0.9% (w/v), from about 0.8% (w/v) to about 1.0% (w/v), from about 0.8% (w/v) to about 1.5% (w/v), from about 0.8% (w/v) to about 2.0% (w/v), from about 0.8% (w/v) to about 2.5% (w/v), from about 0.8% (w/v) to about 3% (w/v), from about 0.8% (w/v) to about 4% (w/v), from about 0.8% (w/v) to about 5% (w/v), from about 0.8% (w/v) to about 7% (w/v), from about 0.8% (w/v) to about 9% (w/v), from about 0.8% (w/v) to about 11% (w/v), from about 0.8% (w/v) to about 13% (w/v), from about 0.8% (w/v) to about 15% (w/v), from about 0.9% (w/v) to about 1.0% (w/v), from about 0.9% (w/v) to about 1.5% (w/v), from about 0.9% (w/v) to about 2.0% (w/v), from about 0.9% (w/v) to about 2.5% (w/v), from about 0.9% (w/v) to about 3% (w/v), from about 0.9% (w/v) to about 4% (w/v), from about 0.9% (w/v) to about 5% (w/v), from about 0.9% (w/v) to about 7% (w/v), from about 0.9% (w/v) to about 9% (w/v), from about 0.9% (w/v) to about 11% (w/v), from about 0.9% (w/v) to about 13% (w/v), from about 0.9% (w/v) to about 15% (w/v), from about 1.0% (w/v) to about 1.5% (w/v), from about 1.0% (w/v) to about 2.0% (w/v), from about 1.0% (w/v) to about 2.5% (w/v), from about 1.0% (w/v) to about 3% (w/v), from about 1.0% (w/v) to about 4% (w/v), from about 1.0% (w/v) to about 5% (w/v), from about 1.0% (w/v) to about 7% (w/v), from about 1.0% (w/v) to about 9% (w/v), from about 1.0% (w/v) to about 11% (w/v), from about 1.0% (w/v) to about 13% (w/v), from about 1.0% (w/v) to about 15% (w/v), from about 1.5% (w/v) to about 2.0% (w/v), from about 1.5% (w/v) to about 2.5% (w/v), from about 1.5% (w/v) to about 3% (w/v), from about 1.5% (w/v) to about 4% (w/v), from about 1.5% (w/v) to about 5% (w/v), from about 1.5% (w/v) to about 7% (w/v), from about 1.5% (w/v) to about 9% (w/v), from about 1.5% (w/v) to about 11% (w/v), from about 1.5% (w/v) to about 13% (w/v), from about 1.5% (w/v) to about 15% (w/v), from about 2.0% (w/v) to about 2.5% (w/v), from about 2.0% (w/v) to about 3% (w/v), from about 2.0% (w/v) to about 4% (w/v), from about 2.0% (w/v) to about 5% (w/v), from about 2.0% (w/v) to about 7% (w/v), from about 2.0% (w/v) to about 9% (w/v), from about 2.0% (w/v) to about 11% (w/v), from about 2.0% (w/v) to about 13% (w/v), from about 2.0% (w/v) to about 15% (w/v), from about 2.5% (w/v) to about 3% (w/v), from about 2.5% (w/v) to about 4% (w/v), from about 2.5% (w/v) to about 5% (w/v), from about 2.5% (w/v) to about 7% (w/v), from about 2.5% (w/v) to about 9% (w/v), from about 2.5% (w/v) to about 11% (w/v), from about 2.5% (w/v) to about 13% (w/v), from about 2.5% (w/v) to about 15% (w/v), from about 3% (w/v) to about 4% (w/v), from about 3% (w/v) to about 5% (w/v), from about 3% (w/v) to about 7% (w/v), from about 3% (w/v) to about 9% (w/v), from about 3% (w/v) to about 11% (w/v), from about 3% (w/v) to about 13% (w/v), from about 3% (w/v) to about 15% (w/v), from about 4% (w/v) to about 5% (w/v), from about 4% (w/v) to about 7% (w/v), from about 4% (w/v) to about 9% (w/v), from about 4% (w/v) to about 11% (w/v), from about 4% (w/v) to about 13% (w/v), from about 4% (w/v) to about 15% (w/v), from about 5% (w/v) to about 7% (w/v), from about 5% (w/v) to about 9% (w/v), from about 5% (w/v) to about 11% (w/v), from about 5% (w/v) to about 15% (w/v), from about 5% (w/v) to about 15% (w/v), from about 7% (w/v) to about 9% (w/v), from about 7% (w/v) to about 11% (w/v), from about 7% (w/v) to about 13% (w/v), from about 7% (w/v) to about 15% (w/v), from about 9% (w/v) to about 11% (w/v), from about 9% (w/v) to about 13% (w/v), from about 9% (w/v) to about 15% (w/v), from about 11% (w/v) to about 13% (w/v), from about 11% (w/v) to about 15% (w/v), from about 13% (w/v) to about 15% (w/v), about 0.1% (w/v), about 0.2% (w/v), about 0.3% (w/v), about 0.4% (w/v), about 0.5% (w/v), about 0.6% (w/v), about 0.7% (w/v), about 0.8% (w/v), about 0.9% (w/v), about 1.0% (w/v), about 1.5% (w/v), about 2.0% (w/v), about 2.5% (w/v), about 3% (w/v), about 4% (w/v), about 5% (w/v), about 7% (w/v), about 9% (w/v), about 11% (w/v), about 13% (w/v), and about 15% (w/v).

The compositions disclosed herein may further comprise a buffering agent. The buffering agent may be an amine or a non-amine compound. In some embodiments, the buffering agent has at least one $pK_a$ selected from the group consisting of: from approximately 7.0 to approximately 9.0, from approximately 7.5 to approximately 9.0, from approximately 8.0 to approximately 9.0, from approximately 8.5 to approximately 9.0, from approximately 7.0 to approximately 8.5, from approximately 7.5 to approximately 8.5, from approximately 8.0 to approximately 8.5, from approximately 7.0 to approximately 8.0, from approximately 7.5 to approximately 8.0, from approximately 7.0 to approximately 7.5, 7.0 or greater, 7.5 or greater, 8.0 or greater, 8.5 or greater, 9.0 or greater, 7.0, 7.1, 7.2, 7.3, 7.4, 7.5, 7.6, 7.7, 7.8, 7.9, 8.0, 8.1, 8.2, 8.3, 8.4, 8.5, 8.6, 8.8, 8.9, 9.0, 9.1, 9.2, 9.3, 9.4, 9.5, 9.6, 9.7, 9.8, and 9.9.

In one embodiment, the amount of buffering agent in the lysis solution is selected from the group consisting of: from about 25 mM to about 50 mM, from about 25 mM to about 75 mM, from about 25 mM to about 100 mM, from about 25 mM to about 125 mM, from about 25 mM to about 130 mM, from about 25 mM to about 135 mM, from about 25 mM to about 140 mM, from about 25 mM to about 145 mM, from about 25 mM to about 150 mM, from about 25 mM to about 155 mM, from about 25 mM to about 160 mM, from about 25 mM to about 165 mM, from about 25 mM to about 170 mM, from about 25 mM to about 175 mM, from about 25 mM to about 200 mM, from about 25 mM to about 225 mM, from about 25 mM to about 250 mM, from about 50 mM to about 75 mM, from about 50 mM to about 100 mM, from about 50 mM to about 125 mM, from about 50 mM to about 130 mM, from about 50 mM to about 135 mM, from about 50 mM to about 140 mM, from about 50 mM to about 145 mM, from about 50 mM to about 150 mM, from about 50 mM to about 155 mM, from about 50 mM to about 160 mM, from about 50 mM to about 165 mM, from about 50 mM to about 170 mM, from about 50 mM to about 175 mM, from about 50 mM to about 200 mM, from about 50 mM to about 225 mM, from about 50 mM to about 250 mM, from about 75 mM to about 100 mM, from about 75 mM to about 125 mM, from about 75 mM to about 130 mM, from about 75 mM to about 135 mM, from about 75 mM to about 140 mM, from about 75 mM to about 145 mM, from about 75 mM to about 150 mM, from about 75 mM to about 155 mM, from about 75 mM to about 160 mM, from about 75 mM to about 165 mM, from about 75 mM to about 170 mM, from about 75 mM to about 175 mM, from about 75 mM to about 200 mM, from about 75 mM to about 225 mM, from about 75 mM to about 250 mM, from about 100 mM to about 125 mM, from about 100 mM to about 130 mM, from about 100 mM to about 135 mM, from about 100 mM to about 140 mM, from about 100 mM to about 145 mM, from about 100 mM to about 150 mM, from about 100 mM to about 155 mM, from about 100 mM to about 160 mM, from about 100 mM to about 165 mM, from about 100 mM to about 170 mM, from about 100 mM to about 175 mM, from about 100 mM to about 200 mM, from about 100 mM to about 225 mM, from about 100 mM to about 250 mM, from about 125 mM to about 130 mM, from about 125 mM to about 135 mM, from about 125 mM to about 140 mM, from about 125 mM to about 145 mM, from about 125 mM to about 150 mM, from about 125 mM to about 155 mM, from about 125 mM to about 160 mM, from about 125 mM to about 165 mM, from about 125 mM to about 170 mM, from about 125 mM to about 175 mM, from about 125 mM to about 200 mM, from about 125 mM to about 225 mM, from about 125 mM to about 250 mM, from about 130 mM to about 135 mM, from about 130 mM to about 140 mM, from about 130 mM to about 145 mM, from about 130 mM to about 150 mM, from about 130 mM to about 155 mM, from about 130 mM to about 160 mM, from about 130 mM to about 165 mM, from about 130 mM to about 170 mM, from about 130 mM to about 175 mM, from about 130 mM to about 200 mM, from about 130 mM to about 225 mM, from about 130 mM to about 250 mM, from about 135 mM to about 140 mM, from about 135 mM to about 145 mM, from about 135 mM to about 150 mM, from about 135 mM to about 155 mM, from about 135 mM to about 160 mM, from about 135 mM to about 165 mM, from about 135 mM to about 170 mM, from about 135 mM to about 175 mM, from about 135 mM to about 200 mM, from about 135 mM to about 225 mM, from about 135 mM to about 250 mM, from about 140 mM to about 145 mM, from about 140 mM to about 150 mM, from about 140 mM to about 155 mM, from about 140 mM to about 160 mM, from about 140 mM to about 165 mM, from about 140 mM to about 170 mM, from about 140 mM to about 175 mM, from about 140 mM to about 200 mM, from about 140 mM to about 225 mM, from about 140 mM to about 250 mM, from about 145 mM to about 150 mM, from about 145 mM to about 155 mM, from about 145 mM to about 160 mM, from about 145 mM to about 165 mM, from about 145 mM to about 170 mM, from about 145 mM to about 175 mM, from about 145 mM to about 200 mM, from about 145 mM to about 225 mM, from about 145 mM to about 250 mM, from about 150 mM to about 155 mM, from about 150 mM to about 160 mM, from about 150 mM to about 165 mM, from about 150 mM to about 170 mM, from about 150 mM to about 175 mM, from about 150 mM to about 200 mM, from about 150 mM to about 225 mM, from about 150 mM to about 250 mM, from about 155 mM to about 160 mM, from about 155 mM to about 165 mM, from about 155 mM to about 170 mM, from about 155 mM to about 175 mM, from about 155 mM to about 200 mM, from about 155 mM to about 225 mM, from about 155 mM to about 250 mM, from about 160 mM to about 165 mM, from about 160 mM to about 170 mM, from about 160 mM to about 175 mM, from about 160 mM to about 200 mM, from about 160 mM to about 225 mM, from about 160 mM to about 250 mM, from about 165 mM to about 170 mM, from about 165 mM to about 175 mM, from about 165 mM to about 200 mM, from about 165 mM to about 225 mM, from about 165 mM to about 250 mM, from about 170 mM to about 175 mM, from about 170 mM to about 200 mM, from about 170 mM to about 225 mM, from about 170 mM to about 250 mM, from about 175 mM to about 200 mM, from about 175 mM to about 225 mM, from about 175 mM to about 250 mM, from about 200 mM to about 225 mM, from about 200 mM to about 250 mM, from about 225 mM to about 250 mM, about 25 mM, about 50 mM, about 75 mM, about 100 mM, about 125 mM, about 130 mM, about 135 mM, about 140 mM, about 145 mM, about 150 mM, about 155 mM, about 160 mM, about 165 mM, about 170 mM, about 175 mM, about 200 mM, about 225 mM, and about 250 mM.

Exemplary buffering agents include without limitation tris (hydroxymethyl)aminomethane ("TRIS") and derivatives thereof, such as N-tris-(hydroxymethyl)methyl-3-aminopropanesulfonic acid ("TAPS"), 3-[N-tris-(hydroxymethyl)-methyl-amino]-2-hydroxypropanesulfonic acid ("TAPSO"); N-tris(hydroxymethyl)methyl-2-aminoethanesulfonic acid ("TES"); N-[tris(hydroxymethyl)methyl]-glycine ("TRICINE"); bis(2-hydroxyethyl)iminotris-(hydroxymethyl) methane ("bis-TRIS"); 1,3-bis[tris(hydroxymethyl)methylamino]propane ("bis-TRIS PROPANE"); carbonate-bicarbonate; glycine; phosphate; 4-(2-hydroxyethyl)-1-piperazineethanesulfonic acid ("HEPES"); N,N-bis(2-hydroxyethyl)glycine ("Bicine"); 3-(N-morpholino) propanesulfonic acid ("MOPS"); and other Good buffers.

In some embodiments, the lysis solution has a pH selected from the group consisting of: from approximately 7.5 to approximately 10, from approximately 7.5 to approximately 9.5, from approximately 8.0 to approximately 9.5, from approximately 8.5 to approximately 9.5, from approximately 9.0 to approximately 9.5, from approximately 7.5 to approximately 9.0, from approximately 8.0 to approximately 9.0, from approximately 8.5 to approximately 9.0, from approximately 7.0 to approximately 8.5, from approximately 7.5 to approximately 8.5, from approximately 8.0 to approximately 8.5, from approximately 7.0 to approximately 8.0, from approximately 7.5 to approximately 8.0, from approximately 7.0 to approximately 7.5, 7.0 or greater, 7.5 or greater, 8.0 or greater, 8.5 or greater, 9.0 or greater, 9.5 or greater, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, and 10.0.

In another embodiment, the composition further comprises a protein digestive enzyme. By way of example and not limitation, the protein digestive enzyme may be Proteinase K, trypsin, pepsin, thermolysin, thrombin, factor Xa, and combinations thereof.

In another embodiment, the lysis solution comprises a preservative. Suitable preservatives include sodium azide, gentomycin, and ProClin®, which is a composition comprising three isothiazolones: 2-Methyl-4-isothiazolin-3-one, 5-Chloro-2-methyl-4-isothiazolin-3-one, and 1,2-Benzisothiazolin-3-one. In one embodiment, the amount of preservative in the lysis solution can be about 0.01%, or about 0.02%, or about 0.03%, or about 0.04%, or about 0.05%, or about 0.06%, or about 0.07%, or about 0.08%, or about 0.09%, or about 0.10%, or about 0.11%, or about 0.12%, or about 0.13%, or about 0.14%, or about 0.15%, or about 0.16%, or about 0.17%, or about 0.18%, or about 0.19%, or about 0.20%.

In another embodiment, the composition further comprises at least one reagent for isolating nucleic acids. By way of example and not limitation, the reagent for isolating nucleic acids can be magnetic beads modified to bind specifically to nucleic acids.

The present disclosure further provides methods of preparing a fixed biological sample for molecular analysis comprising lysing the fixed biological sample in the presence of composition comprising at least two amines to create a lysate; and isolating a component of the lysate.

Any manner of lysing the fixed biological sample can be used in the disclosed method, including without limitation: mechanical lysis, such as by sonication or cytolysis; and chemical lysis, including use of detergents such as 3-[(3 cholamidopropyl)dimethylammonio]-1-propanesulfonate (sold commercially as CHAPS), NONIDET P-40 (also known as Igepal CA-630), deoxycholate, TRITON X-100 (also known as 4-(1,1,3,3-Tetramethylbutyl)phenyl-polyethylene glycol), sodium dodecyl sulfate (sold commercially as SDS), and/or polysorbate surfactants (sold commercially as TWEEN).

In a further embodiment, the lysis step of the disclosed method is performed in the presence of heat.

In a further embodiment, the composition comprising at least two amines has a basic pH value. In a further embodiment, the pH value is greater than 7.5. In a further embodiment, the pH value is greater than 8. In a further embodiment, the pH value is greater than 8.5. In a further embodiment, the pH value is greater than 9. In a further embodiment, the pH value is between approximately 8.0 and approximately 10. In a further embodiment, the pH value is between approximately 9 and approximately 10. In a further embodiment, the pH value is between approximately 8.5 and approximately 9.5. In a further embodiment, the pH value is between approximately 9 and approximately 9.5.

In a further embodiment, the lysis step is performed in the presence of a protein digestive enzyme. An exemplary protein digestive enzymes includes, but is not limited to, Proteinase K, trypsin, pepsin, thermolysin, thrombin, factor Xa, and combinations thereof.

In one embodiment, the component of the lysate that is isolated is an organelle. Exemplary organelles that may be isolated include, but are not limited to nuclei, ribosomes, plasma membranes, endoplasmic reticulum, mitochondria, Golgi apparatus, lysosomes, vacuoles, and vesicles.

In one embodiment, the component of the lysate that is isolated is a nucleic acid. Any form of nucleic acid can be recovered using the disclosed methods and reagents, including but not limited to nuclear DNA, mitochondrial DNA, mRNA, chromatin, chromosomal DNA, exogenous plasmids, viral DNA, viral RNA, bacterial DNA, and bacterial RNA.

Nucleic acid recovery methods include without limitation: chromatography, including but not limited to silica or glass adsorption, ion exchange chromatography, affinity purification, spin column chromatography, and gel filtration; solvent extraction and precipitation; and centrifugation. Nucleic acid recovery methods include without limitation ammonium sulfate precipitation, differential solubilization, sucrose gradient centrifugation, and chromatography. By way of example and not limitation, the nucleic acid may be isolated by using magnetic beads modified to bind specifically to nucleic acids.

In another embodiment, a nucleic acid comprising a specific sequence may be isolated by hybridizing it to a nucleic acid probe complementary to the specific sequence. In one embodiment, the nucleic acid probe is bound to a solid phase or adapted to be bound to a solid phase. In another embodiment, hybridization of the nucleic acid probe to the nucleic acid molecule results in a DNA:RNA hybrid between the probe and the nucleic acid molecule. The resulting hybrid may then be bound by an antibodies known to bind specifically to DNA:RNA hybrids ("DNA:RNA-binding antibody"), which in turn may be bound to a solid phase or adapted to be bound to a solid phase. In either case, hybridization of the probe with the nucleic acid results in the nucleic acid being associated with a solid phase, which may then be separated from the lysate using mechanical means. By way of example and not limitation, such methods are described in U.S. Pat. No. 6,228,578 and U.S. patent application Ser. No. 12/695,071, the contents of which are incorporated in their entirety by reference. Exemplary DNA:RNA-binding antibodies include, but are not limited to, those disclosed in U.S. Pat. Nos. 4,732,847 and 4,865,980, the contents of which are incorporated herein by reference in their entireties.

By way of example, and not limitation, an appropriate solid phase includes, but is not limited to: silica, borosilicates, silicates, anorganic glasses, organic polymers such as poly(meth)acrylates, polyurethanes, polystyrene, agarose, polysaccharides such as cellulose, metal oxides such as aluminum oxide, magnesium oxide, titanium oxide and zirconium oxide, metals such as gold or platinum, agarose, sephadex, sepharose, polyacrylamide, divinylbenzene polymers, styrene divinylbenzene polymers, dextrans, and derivatives thereof, and/or silica gels, beads, membranes, and resins; glass or silica surfaces, such as beads, plates, and capillary tubes; magnetizable or magnetic (e.g. paramagnetic, superparamagnetic, ferromagnetic or ferrimagnetic) particles, including but not limited to polystyrene, agarose, polyacrylamide, dextran, and/or silica materials having a magnetic material incorporated therein or associated therewith. In some exemplary embodiments, the nucleic acid probe or antibody can be linked to the surface of a processing vessel such as a micro-tube, a well of micro-plate, or capillary, and using these surfaces the nucleic acid can be isolated on a micro scale. Where a biotinylated nucleic acid probe or antibody is provided, the solid phase may be coated with a substance capable of binding the biotin moiety, such as, for example, avidin, streptavidin, and/or neutravidin. In another embodiment, the solid phase may be coated with, or adapted to be coated with, an antibody specific for a DNA:RNA hybrid.

Nucleic acids obtained using the disclosed methods and compositions may be used in subsequent molecular analytical methods including without limitation gel electrophoresis, PCR-related techniques including reverse transcriptase PCR and real time PCR, sequencing, sub-cloning procedures, Southern blotting, northern blotting, fluorescent in situ hybridization, and various mutational analyses including hybrid capture and multiplex analysis.

In one embodiment, the component of the lysate that is isolated is a protein. Protein recovery methods include without limitation ammonium sulfate precipitation, differential solubilization, sucrose gradient centrifugation, and chromatography. Chromatographic protein isolation methods include without limitation size exclusion, ion exchange, hydrophobic interaction, affinity, immuno-affinity, and metal binding chromatography.

Proteins obtained with the disclosed methods and compositions may be used in subsequent molecular analytical methods including without limitation sequencing, immunoprecipitation, western blots, ELISA assays, dot blots, and enzyme assay The methods described also can be used to isolate pathogens, including without limitation bacteria, fungi, yeast, protozoa, prions, and viruses.

The methods and compositions described herein are easily and rapidly optimized for specimens preserved in either cross-linking or precipitating fixatives.

The methods and compositions described herein also are adaptable for all biological fluids and provide to simple protocols that are proven compatible with high throughput automation, including for example the QIAensemble® Next Gen™ Sample Processor, an automated sample processing device for extraction and analysis which provides full automation, including de-capping and capping of specimens and zero ergonomic movements. As such, they provide for ultra high through-put and ecologically friendly sample processing by allowing for a flexible input volume, non-hazardous material liquid waste, limited solid waste, and reagents that may be stored at room temperature.

EXAMPLES

Example 1

This following example shows the effect of various lysis solutions on the yield and signal sensitivity of HPV DNA isolated from aldehyde-fixed clinical cervical samples.

Figure 1B:
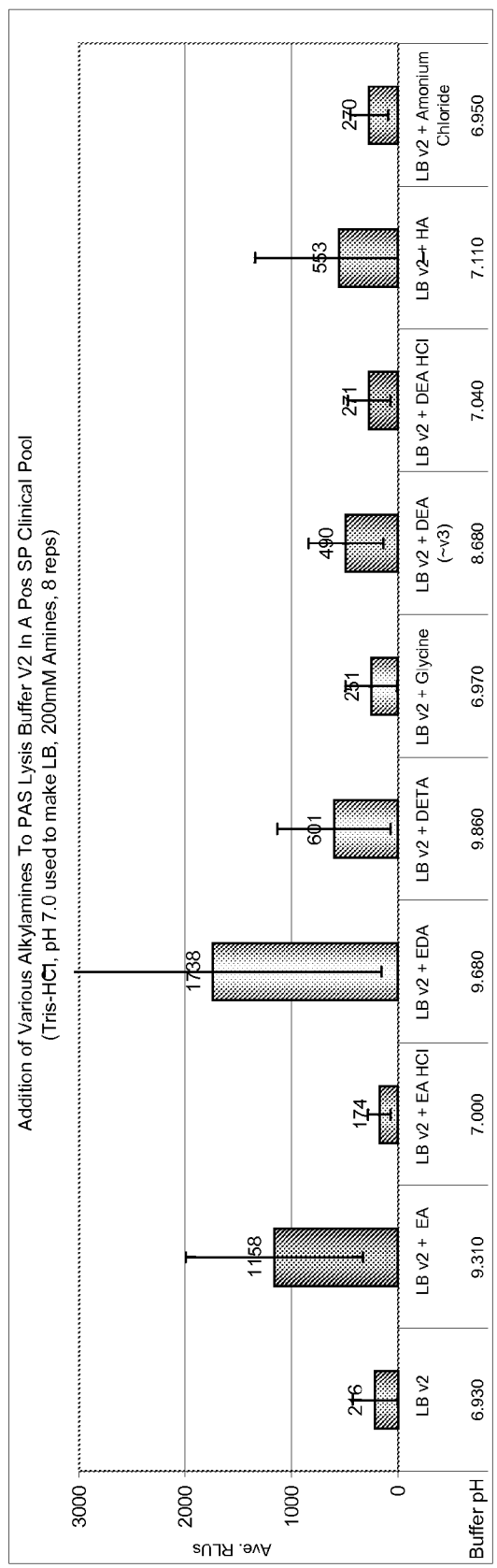

Clinical cervical samples were collected and fixed in SUREPATH fixative. The fixed samples were then washed and suspended in a lysis solution ("LB") of: (1) 3% (v/v) Brij-58, and (2) 150 mM Tris-HCl. An additional amine selected from the following group was added to test samples at a concentration of 200 mM: diethanolamine ("DEA"), triethanolamine ("TEA"), TEA-HCl, triethylamine ("TE"), DEA plus indium (III) chloride ("IC"), dicyandiamide ("DC"), DEA plus magnesium perchlorate ("Mg(ClO$_4$)$_2$"); hexamethylene-tetramine ("HMTA"), DEA plus palladium (II) acetate ("PA"), diethylenetriamine ("DETA"), ethylenediamine ("EDA"), glycine, hydroxylamine ("HA"), and ammonium chloride. Typically, 1.5 mL of the sample is added to 1 mL of lysis buffer, plus 25 µl of Proteinase K (10 mg/ml stock) and 60 µl of 1.5% (v/v) AxpH™ DNA-affinity magnetic beads to lyse. A magnetic field was applied to the tubes and the lysate was removed, leaving only the magnetic beads. DNA was eluted from the beads and the presence of HPV DNA was determined using a hybrid capture method as described in U.S. Pat. No. 6,228,578, the contents of which are incorporated in their entirety by reference. Results are shown in Tables 1 and 2 and FIGS. 1A and 1B. Shaded cells in tables 1 and 2 indicate replicates wherein RLU/CO is greater than 1.00.

Tables 1 and 2 show raw data from each replicate (RLU/CO) and combined data for each lysis solution tested. The combined data set is displayed graphically at FIGS. 1A and 1B. As can be seen, the addition of an amine-containing compound to a Tris-buffered lysis solution increased the sensitivity of detection of the HPV DNA in the cervical samples.

TABLE 1

|  | LB | LB + DEA | LB + TEA | LB + TEA-HCl | LB + TE | LB + DEA-IC | LB + DC | LB + DEA + Mg(ClO$_4$)$_2$ | LB + HMTA | LB + DEA + PA |
|---|---|---|---|---|---|---|---|---|---|---|
| pH | 6.890 | 8.700 | 8.060 | 6.400 | 10.050 | 7.530 | 6.910 | 8.750 | 6.990 | 8.470 |
| RLU/CO | 0.20 | 1.46 | 7.19 | 0.81 | 1.25 | 0.29 | 2.92 | 2.52 | 1.08 | 0.15 |
|  | 0.70 | 2.16 | 14.29 | 1.00 | 6.61 | 0.28 | 1.52 | 3.14 | 0.57 | 0.18 |
|  | 0.55 | 2.69 | 1.86 | 0.54 | 0.50 | 0.25 | 0.89 | 0.60 | 0.34 | 0.19 |
|  | 2.15 | 9.09 | 1.40 | 0.67 | 0.55 | 0.24 | 1.22 | 0.74 | 1.06 | 0.21 |
|  | 0.74 | 6.98 | 2.41 | 1.28 | 0.57 | 0.18 | 1.52 | 0.54 | 1.31 | 0.17 |
|  | 0.44 | 11.58 | 6.08 | 0.55 | 0.48 | 0.23 | 3.70 | 0.47 | 2.92 | 0.21 |
|  | 0.95 | 4.46 | 2.69 | 1.13 | 1.27 | 0.18 | 0.64 | 2.88 | 0.80 | 0.16 |
|  | 0.50 | 11.59 | 14.22 | 1.82 | 0.41 | 0.15 | 5.22 | 2.01 | 0.56 | 0.20 |
| Ave. RLU | 169 | 1354 | 1357 | 211 | 315 | 49 | 477 | 349 | 234 | 40 |
| Std. Dev. RLU | 129 | 900 | 1155 | 94 | 457 | 11 | 346 | 248 | 175 | 5 |
| CV % | 76.5% | 66.5% | 85.1% | 44.7% | 145.1% | 21.6% | 72.7% | 71.0% | 74.8% | 13.8% |
| Ave. RLU/CO | 0.78 | 6.25 | 6.27 | 0.97 | 1.45 | 0.23 | 2.20 | 1.61 | 1.08 | 0.18 |
| Std. Dev. of RLU/CO | 0.60 | 4.16 | 5.34 | 0.44 | 2.11 | 0.05 | 1.60 | 1.15 | 0.81 | 0.03 |
| Fold increase | 1.00 | 8.01 | 8.03 | 1.25 | 1.86 | 0.29 | 2.82 | 2.07 | 1.39 | 0.24 |

TABLE 2

|  | LB | LB + EA | LB + EA HCl | LB + EDA | LB + DETA | LB + glycine | LB + DEA | LB + DEA HCl | LB + HA | LB + Ammonium chloride |
|---|---|---|---|---|---|---|---|---|---|---|
| pH | 6.930 | 9.310 | 7.000 | 9.680 | 9.860 | 6.970 | 8.680 | 7.040 | 7.110 | 6.950 |
| RLU/CO | 0.36 | 7.73 | 0.33 | 0.53 | 2.45 | 0.89 | 1.50 | 0.33 | 1.19 | 1.29 |
|  | 0.91 | 1.07 | 1.43 | 17.95 | 2.03 | 3.20 | 0.68 | 0.33 | 9.62 | 0.50 |
|  | 0.46 | 8.96 | 0.72 | 2.28 | 1.66 | 0.96 | 1.29 | 0.87 | 1.10 | 0.83 |
|  | 2.77 | 1.49 | 0.26 | 10.58 | 0.51 | 0.56 | 2.89 | 2.52 | 1.37 | 0.26 |
|  | 0.28 | 2.48 | 0.40 | 10.50 | 1.30 | 0.51 | 0.46 | 0.62 | 1.12 | 1.17 |
|  | 0.67 | 5.59 | 1.03 | 3.24 | 3.01 | 0.87 | 4.53 | 0.71 | 0.89 | 0.54 |
|  | 0.43 | 6.88 | 0.79 | 7.27 | 6.91 | 0.40 | 1.23 | 1.08 | 1.24 | 1.28 |
|  | 0.74 | 1.37 | 0.39 | 1.03 | 0.58 | 0.31 | 2.47 | 1.85 | 0.44 | 2.43 |
| Ave. RLU | 216 | 1158 | 174 | 1738 | 601 | 251 | 490 | 271 | 553 | 270 |
| Std. Dev. of RLU | 212 | 834 | 106 | 1581 | 534 | 243 | 351 | 201 | 792 | 178 |
| CV % | 98.2% | 72.0% | 61.1% | 91.0% | 88.8% | 97.0% | 71.7% | 74.4% | 143.3% | 65.9 |
| Ave. RLU/CO | 0.83 | 4.45 | 0.67 | 6.67 | 2.31 | 0.96 | 1.88 | 1.04 | 2.12 | 1.04 |
| Std. Dev. of RLU/CO | 0.81 | 3.20 | 0.41 | 6.07 | 2.05 | 0.93 | 1.35 | 0.77 | 3.04 | 0.68 |

In addition, Table 3 shows the effect of addition of 200 mM diethanolamine on 26 individual clinical cervical samples. In each case, the addition of diethanolamine led to an increase in the sensitivity, ranging from a 1.01-fold increase to a 13.46-fold increase.

TABLE 3

| SP Sample ID | no DEA | 200 mM DEA | Fold Increase |
|---|---|---|---|
| SP 005657 | 46.41 | 406.20 | 8.75 |
| SP 005514 | 1.17 | 1.44 | 1.23 |
| SP 005864 | 0.48 | 4.55 | 9.49 |
| SP 005609 | 126.36 | 203.74 | 1.61 |
| SP 005618 | 190.33 | 316.37 | 1.66 |
| SP 005520 | 361.16 | 366.03 | 1.01 |
| SP 005548 | 12.94 | 32.98 | 2.55 |
| SP 005513 | 207.63 | 238.05 | 1.15 |
| SP 005572 | 117.53 | 203.80 | 1.73 |
| SP 005554 | 8.37 | 11.49 | 1.37 |
| SP 005567 | 1.53 | 20.52 | 13.46 |
| SP 005828 | 5.66 | 13.84 | 2.45 |
| SP 005614 | 5.40 | 17.14 | 3.17 |

TABLE 3-continued

| SP Sample ID | no DEA | 200 mM DEA | Fold Increase |
|---|---|---|---|
| SP 005586 | 332.09 | 495.56 | 1.49 |
| SP 005594 | 6.00 | 34.68 | 5.78 |
| SP 005495 | 15.33 | 25.80 | 1.68 |
| SP 005569 | 139.73 | 261.65 | 1.87 |
| SP 005755 | 0.55 | 2.79 | 5.08 |
| SP 005470 | 363.91 | 604.78 | 1.66 |
| SP 005475 | 322.91 | 505.12 | 1.56 |
| SP 005477 | 165.55 | 243.46 | 1.47 |
| SP 005399 | 42.07 | 116.67 | 2.77 |
| SP 005611 | 0.85 | 6.86 | 8.11 |
| SP 005482 | 2.34 | 3.90 | 1.67 |
| SP 006011 | 1.44 | 7.81 | 5.43 |
| SP 006014 | 1.02 | 1.52 | 1.49 |

Example 2

This example shows the effect that varying the concentration of Tris has on the increased efficiency of lysis solution comprising both Tris and diethanolamine.

Figure 2:
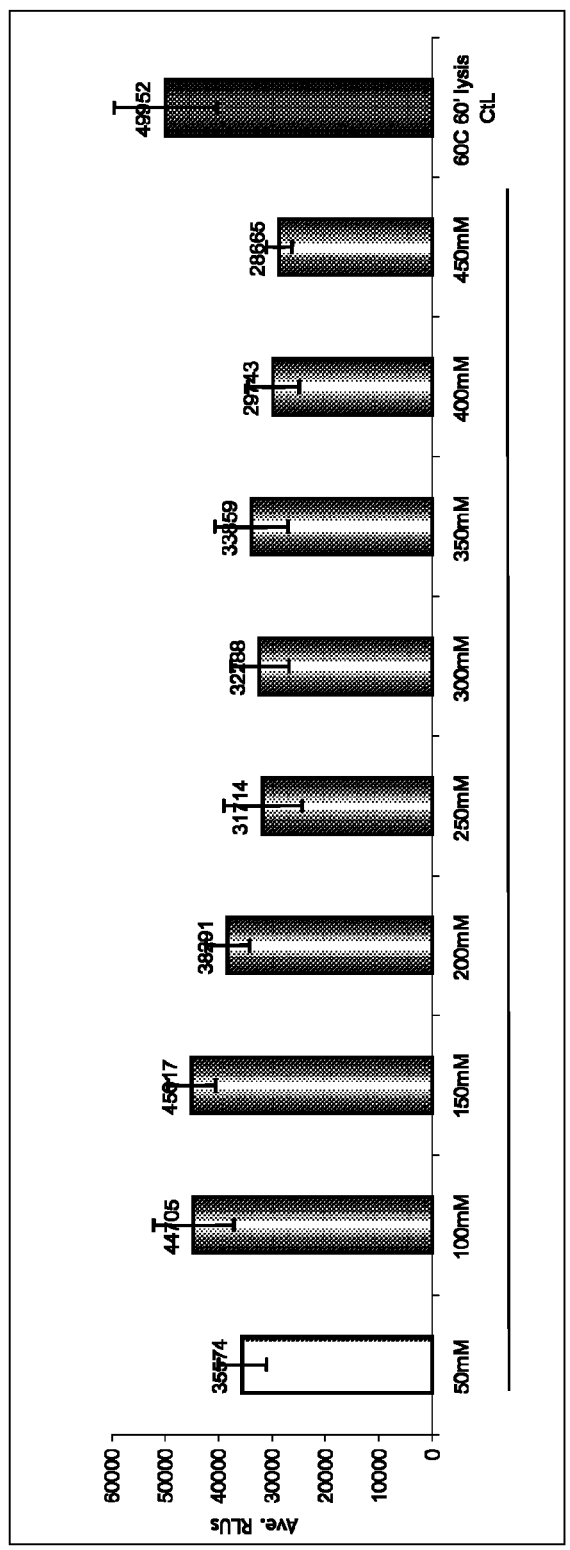
FIG. 2 shows the effect of varying the concentration of Tris-HCl on the efficiency of a lysis solution comprising 300 mM diethanolamine. The labels in the x-axis of the graph indicate the concentration of Tris-HCl in each sample. Columns represent average relative light unit (RLU), with error bars representing the standard deviation of the eight replicates tested.

Analysis was performed in substantially the same was as in Example 1, except the lysis solution comprised (1) 3% (v/v) Brij-58; (2) 300 mM diethanolamine; and (3) Tris at a concentration selected from 50 mM, 100 mM, 150 mM, 200 mM, 250 mM, 300 mM, 350 mM, 400 mM, and 450 mM. Typically, 1.5 mL of the sample is added to 1 mL of lysis buffer, plus 25 μl of Proteinase K (10 mg/ml stock) and 60 μl of 1.5% (v/v) AxpH™ DNA-affinity magnetic beads to lyse. The lysis solution comprising 50 mM TRIS was selected as a baseline for analysis. Results are shown in FIG. 2 and below at Table 4. Shaded cells in Table 4 indicate replicates having an RLU/CO of greater than or equal to 110.

TABLE 4

| Tris HCL (mM) | 50 | 100 | 150 | 200 | 250 | 300 | 350 | 400 | 450 | 60° C. 60' lysis CtL |
|---|---|---|---|---|---|---|---|---|---|---|
| RLU/CO | 94.66 | 109.10 | 138.98 | 111.88 | 63.49 | 80.12 | 115.31 | 92.74 | 79.73 | 128.37 |
| | 107.81 | 107.47 | 121.70 | 107.62 | 79.80 | 89.76 | 84.62 | 76.55 | 90.95 | 148.43 |
| | 105.69 | 126.75 | 137.94 | 122.48 | 94.77 | 134.29 | 77.53 | 102.08 | 101.26 | 134.94 |
| | 120.55 | 169.81 | 159.89 | 130.26 | 84.07 | 105.06 | 118.02 | 114.87 | 88.02 | 166.88 |
| | 112.54 | 143.78 | 120.35 | 142.79 | 113.92 | 84.82 | 82.62 | 71.25 | 78.39 | 176.96 |
| | 138.73 | 166.23 | 151.19 | 118.31 | 109.72 | 101.10 | 108.73 | 90.80 | 86.80 | 214.95 |
| | 99.74 | 145.48 | 149.31 | 104.13 | 105.09 | 99.09 | 137.76 | 106.05 | 90.94 | 129.11 |
| | 102.73 | 140.32 | 137.34 | 112.38 | 135.85 | 106.70 | 115.33 | 83.45 | 95.00 | 139.74 |
| Ave. RLU | 35574 | 44705 | 45017 | 38291 | 31714 | 32288 | 33859 | 29743 | 28665 | 49952 |
| Std. Dev. of RLU | 4494 | 7508 | 4461 | 4134 | 7314 | 5422 | 6831 | 4824 | 2432 | 9647 |
| CV % | 12.6% | 16.8% | 9.9% | 10.8% | 23.1% | 16.8% | 20.2% | 16.2% | 8.5% | 19.3% |
| Ave. RLU/CO | 110.31 | 138.62 | 139.59 | 118.73 | 98.34 | 100.12 | 104.99 | 92.22 | 88.88 | 154.89 |
| Std. Dev. of RLU | 13.94 | 23.28 | 13.83 | 12.82 | 22.68 | 16.81 | 21.18 | 14.96 | 7.54 | 29.91 |
| Fold increase | 1.00 | 1.26 | 1.27 | 1.08 | 0.89 | 0.91 | 0.95 | 0.84 | 0.81 | 1.40 |

Example 3

This example shows the effect of varying the pH on the sensitivity efficiency of nucleic acid lysis solutions comprising both TRIS and diethanolamine.

Figure 3:
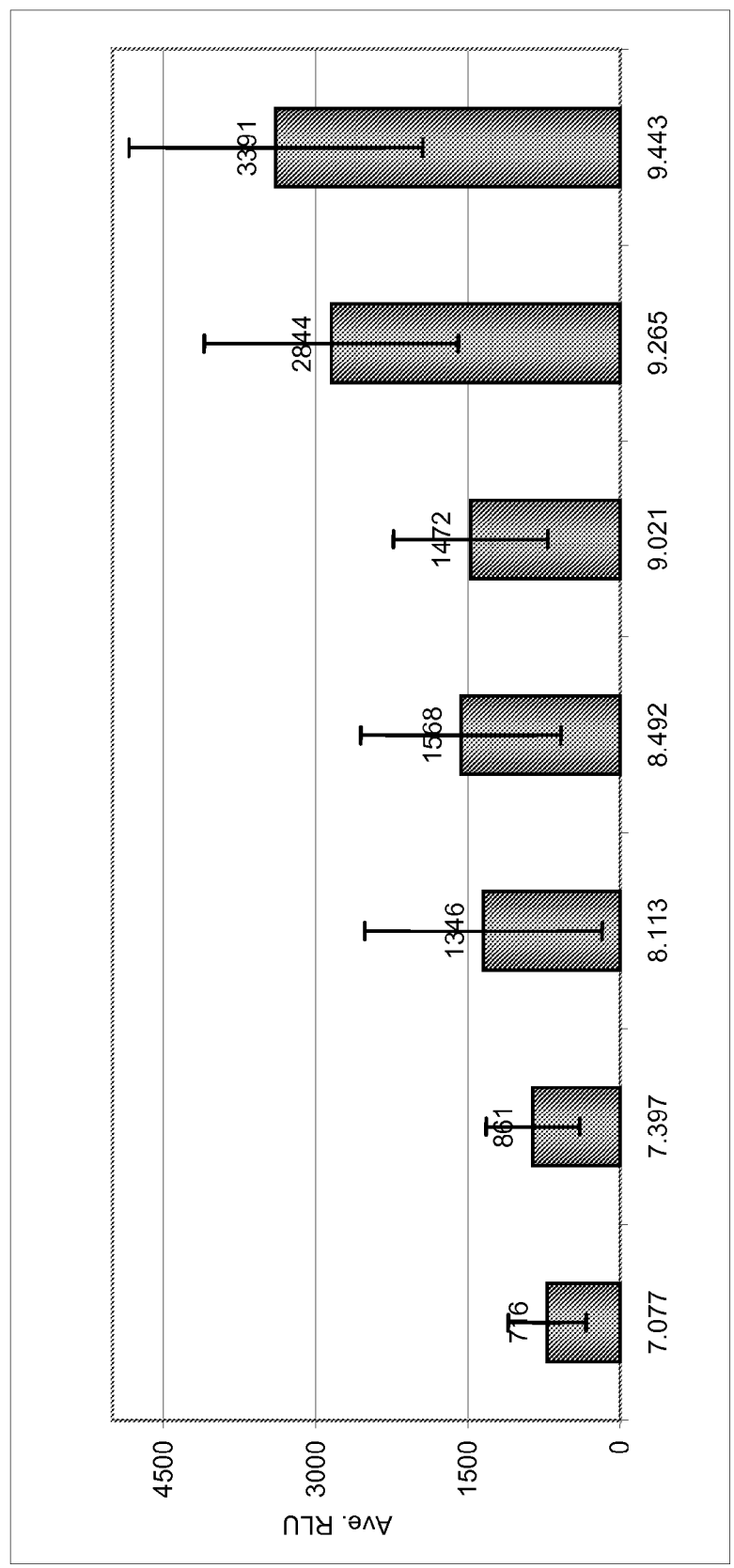
FIG. 3 shows the effect of pH on HPV DNA detection in DNA isolated from aldehyde-fixed cervical samples using a lysis solution comprising 150 mM Tris and 300 mM diethanolamine. The labels in the x-axis of the graph indicate the pH of the lysis solution used. Columns represent average relative light unit (RLU), with error bars representing the standard deviation of the eight replicates tested.

Analysis was performed in substantially the same way as in Example 1, except the lysis solution comprised (1) 3% (v/v) Brij-58; (2) 300 mM diethanolamine; and (3) 150 mM Tris. Typically, 1.5 mL of the sample is added to 1 mL of lysis buffer, plus 250 of Proteinase K (10 mg/ml stock) and 600 of 1.5% (v/v) AxpH™ DNA-affinity magnetic beads to lyse. The pH of the lysis solution was adjusted to a value of 7.077, 7.397, 8.113, 8.492, 9.021, 9.265, and 9.443. Results are shown in FIG. 3 and Table 5. Shaded cells in Table 5 indicate individual replicates with an RLU/CO of greater than or equal to 2.00. As can be seen, increasing the pH value of the lysis solution increased the sensitivity of HPV DNA detection.

TABLE 5

| pH | 7.007 | 7.397 | 8.113 | 8.492 | 9.021 | 9.265 | 9.443 |
|---|---|---|---|---|---|---|---|
| RLU/CO | 1.31 | 3.49 | 1.49 | 1.27 | 4.25 | 7.07 | 11.72 |
| | 1.31 | 2.89 | 1.73 | 1.63 | 3.24 | 10.17 | 4.59 |
| | 2.73 | 2.01 | 2.53 | 7.67 | 2.01 | 7.64 | 5.48 |
| | 1.89 | 2.93 | 2.50 | 5.20 | 3.06 | 11.25 | 8.47 |
| | 0.86 | 1.08 | 2.17 | 3.51 | 8.45 | 5.10 | 5.23 |
| | 3.95 | 4.47 | 8.75 | 3.14 | 4.54 | 2.78 | 15.16 |
| | 2.70 | 1.16 | 1.52 | 3.42 | 1.93 | 13.18 | 11.50 |
| | 1.09 | 1.00 | 9.08 | 8.86 | 5.10 | 5.75 | 12.90 |
| Ave. RLU | 716 | 861 | 1346 | 1568 | 1472 | 2844 | 3391 |
| Std. Dev. of RLU | 384.8 | 460.7 | 1168.9 | 985.3 | 761.2 | 1250.4 | 1446.0 |
| CV % | 53.8% | 53.5% | 86.9% | 62.8% | 51.7% | 44.0% | 42.6% |
| Ave. RLU/CO | 1.98 | 2.38 | 3.72 | 4.34 | 4.07 | 7.87 | 9.38 |
| Std. Dev. of RLU/CO | 1.06 | 1.27 | 3.23 | 2.73 | 2.11 | 3.46 | 4.00 |

Example 4

This example shows the effect of varying the concentration of amine on the sensitivity and efficiency of nucleic acid isolation using a lysis solution comprising both Tris and diethanolamine.

Figure 4:
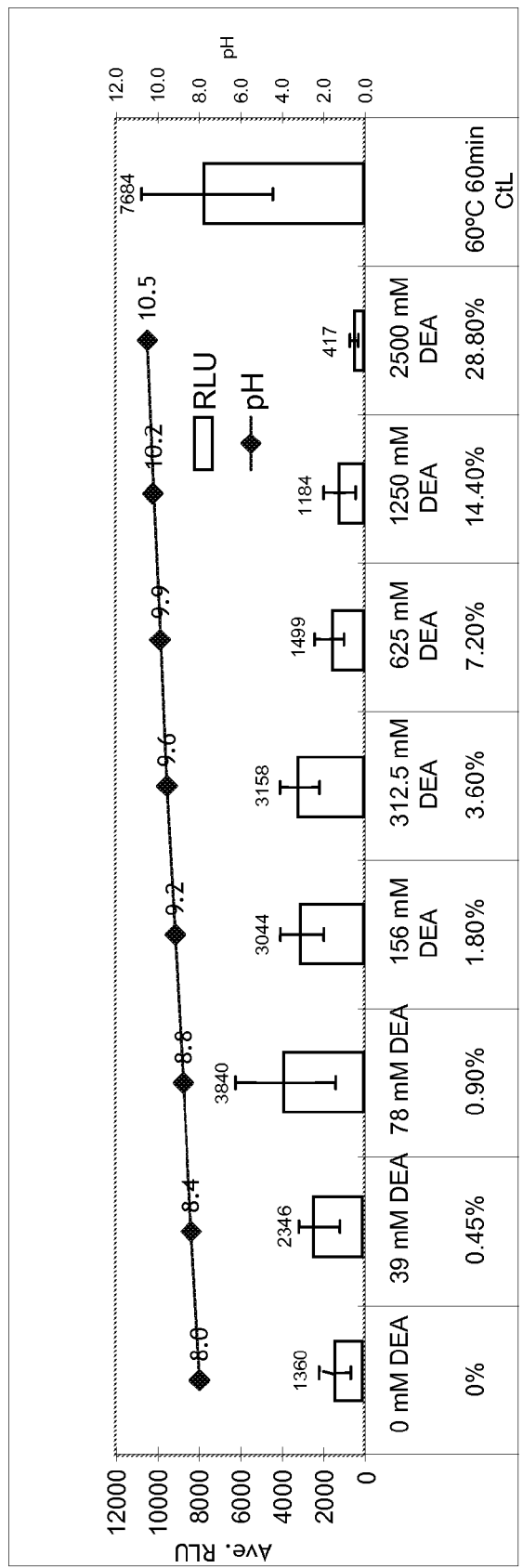
FIG. 4 shows the effect of varying the concentration of diethanolamine on HPV DNA detection in DNA isolated from aldehyde-fixed cervical samples using a lysis solution comprising 150 mM Tris. The top table shows raw data from each replicate for each lysis solution tested. The lower table shows combined data for each lysis solution tested and is displayed graphically in the bar graph at the bottom. The labels in the x-axis of the graph indicate the pH of the lysis solution used. Columns represent average relative light unit (RLU), with error bars representing the standard deviation of the eight replicates tested. The pH of each lysis solution is also displayed on the graph. Control conditions are the same as the test conditions absent the diethanolamine.

Analysis was performed in substantially the same way as in Example 1, except the lysis solution comprised (1) 3% (v/v) Brij-58; (2) 150 mM Tris; and (3) diethanolamine at a concentration selected from: 0 mM, 39 mM, 78 mM, 156 mM, 312.5 mM, 625 mM, 1250 mM, and 2500 mM. The control (CTL) comprised only buffer. Typically, 1.5 mL of the sample is added to 1 mL of lysis buffer, plus 25 µl of Proteinase K (10 mg/ml stock) and 60 µl of 1.5% (v/v) AxpH™ DNA-affinity magnetic beads to lyse. Results are shown in FIG. 4 and Table 6.

TABLE 6

| DEA Conc. | mM | 0 | 39 | 78 | 156 | 312.5 | 625 | 1250 | 2500 | 60° C. 60' lysis CtL |
|---|---|---|---|---|---|---|---|---|---|---|
| | % | 0 | 0.45 | 0.90 | 1.80 | 3.60 | 7.20 | 14.40 | 28.80 | |
| pH | | 7.983 | 8.391 | 8.765 | 9.164 | 9.560 | 9.868 | 10.191 | 10.502 | 6.990 |
| RLU/CO | | 2.28 | 8.59 | 26.65 | 7.40 | 14.38 | 8.14 | 6.82 | 2.64 | 34.41 |
| | | 4.84 | 9.50 | 7.84 | 13.24 | 9.60 | 7.03 | 2.63 | 0.60 | 13.40 |
| | | 6.09 | 6.22 | 8.65 | 12.89 | 6.95 | 3.47 | 3.25 | 2.38 | 35.47 |
| | | 11.03 | 3.15 | 7.11 | 12.49 | 12.89 | 1.36 | 6.69 | 0.90 | 36.74 |
| | | 3.19 | 9.66 | 30.22 | 17.19 | 7.60 | 7.77 | 1.69 | 1.95 | 25.95 |
| | | 3.73 | 12.29 | 12.20 | 5.28 | 16.63 | 4.52 | 2.17 | 1.76 | 47.88 |
| | | 5.41 | 6.58 | 16.11 | | 15.75 | 9.06 | 9.94 | 0.77 | 12.52 |
| | | 4.73 | 15.22 | 7.77 | 12.37 | 12.06 | 4.15 | 2.76 | 1.65 | 26.90 |
| Ave. RLU | | 1360 | 2346 | 3840 | 3044 | 3158 | 1499 | 1184 | 417 | 7684 |
| Std. Dev. of RLU | | 703 | 986 | 2401 | 1046 | 958 | 711 | 779 | 200 | 3174 |
| CV % | | 51.7% | 42.0% | 62.5% | 34.4% | 30.3% | 47.4% | 65.8% | 47.9% | 41.3% |
| Ave. RLU/CO | | 5.16 | 8.90 | 14.57 | 11.55 | 11.98 | 5.69 | 4.49 | 1.58 | 29.16 |
| Std. Dev. of RLU/CO | | 2.67 | 3.74 | 9.11 | 3.97 | 3.64 | 2.70 | 2.96 | 0.76 | 12.05 |

Example 5

Figure 5:
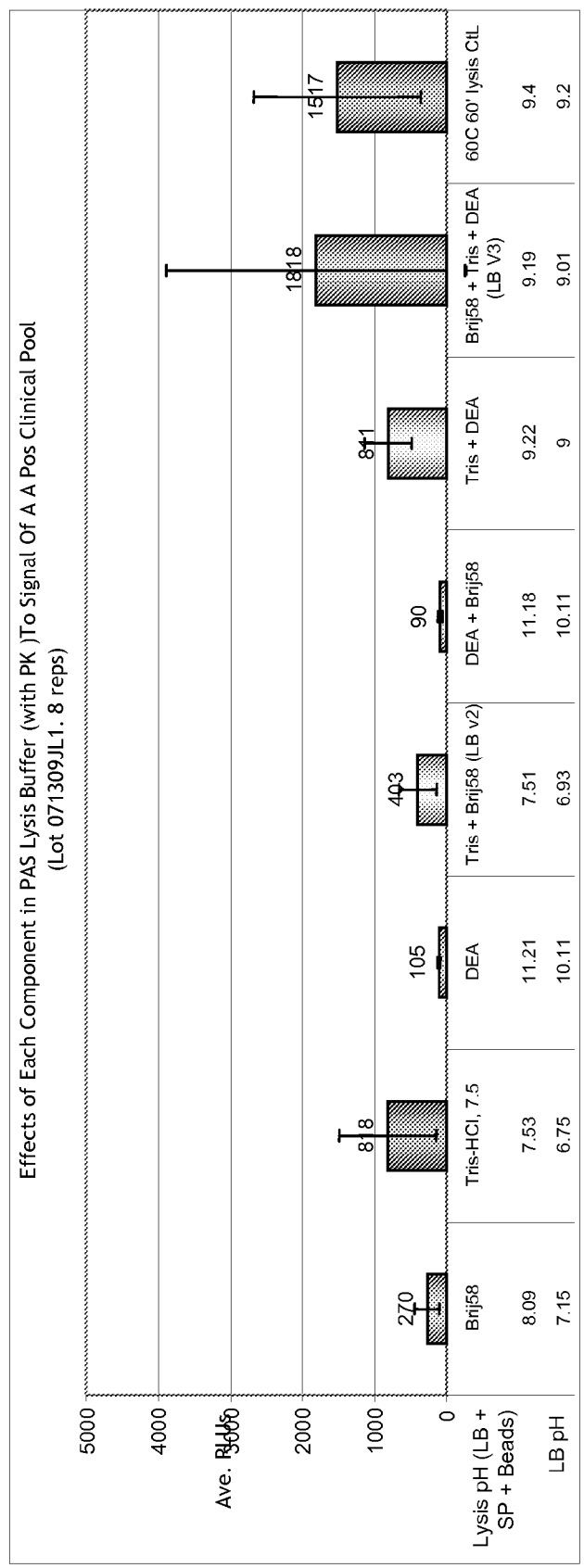
FIG. 5 shows the effects of detergent, Tris, and diethanolamine on extraction and detection of HPV DNA in aldehyde-fixed cervical samples. The top table shows raw data from each replicate for each lysis solution tested. The lower table shows combined data for each lysis solution tested and is displayed graphically in the bar graph at the bottom. The labels in the x-axis of the graph indicate the pH of the lysis solution used. Columns represent average relative light unit (RLU), with error bars representing the standard deviation of the eight replicates tested. The pH of each lysis solution is also displayed on the graph.

This example shows the relative contributions of detergent and each amine. Analysis was performed in substantially the same way as in Example 1, except seven lysis solutions were used: (1) 3% (v/v) Brij-58; (2) 150 mM Tris-HCl; (3) 150 mM diethanolamine; (4) Brij-58 plus 150 mM Tris-HCl; (5) Brij-58 plus 150 mM diethanolamine; (6) 150 mM Tris plus 150 mM diethanolamine; and (7) Brij-58 plus 150 mM Tris plus 150 mM diethanolamine. The control (CTL) comprised only buffer. Typically, 1.5 mL of the sample is added to 1 mL of lysis buffer, plus 25 µl of Proteinase K (10 mg/ml stock) and 60 µl of 1.5% (v/v) AxpH™ DNA-affinity magnetic beads to lyse. Results are shown in FIG. 5 and at Table 7. Shaded cells in Table 7 indicate replicates having an RLU/CO of greater than 1.00.

TABLE 7

| | | Brij58 | Tris-HCl, 7.5 | DEA | Tris + Brij58 | DEA + Brij58 | Tris + DEA | Brij58 Tris + DEA | 60° C. 60' lysis CtL |
|---|---|---|---|---|---|---|---|---|---|
| pH | LB + SP + Beads | 7.15 | 6.75 | 10.11 | 6.93 | 10.11 | 9 | 9.01 | 9.2 |
| | PAS LB | 8.09 | 7.53 | 11.21 | 7.51 | 11.18 | 9.22 | 9.19 | 9.4 |
| | RLU/CO | 1.10 | 6.49 | 0.72 | 0.97 | 0.71 | 7.31 | 2.94 | 5.19 |
| | | 0.55 | 6.07 | 0.41 | 1.50 | 0.34 | 3.44 | 1.99 | 16.86 |
| | | 0.70 | 3.01 | 0.60 | 1.30 | 0.59 | 3.74 | 1.33 | 4.96 |
| | | 1.02 | 1.11 | 0.48 | 1.67 | 0.37 | 4.47 | 8.35 | 2.74 |
| | | 2.82 | 1.12 | 0.48 | 2.05 | 0.34 | 3.91 | 9.08 | |
| | | 2.52 | 2.79 | 0.42 | 1.27 | 0.60 | 4.44 | 32.88 | |
| | | 0.97 | 10.22 | 0.59 | 4.98 | 0.35 | 2.56 | 7.49 | |
| | | 0.89 | 1.24 | 0.42 | 2.08 | 0.23 | 1.97 | 7.24 | |
| Ave. RLU | | 270 | 818 | 105 | 403 | 90 | 811 | 1818 | 1517 |
| Std. Dev. of RLU | | 174 | 671 | 23 | 259 | 35 | 327 | 2070 | 1160 |
| CV % | | 64.6% | 82.1% | 22.1% | 64.3% | 38.5% | 40.3% | 113.9% | 76.5% |
| Ave. RLU/CO | | 1.32 | 4.01 | 0.51 | 1.98 | 0.44 | 3.98 | 8.91 | 7.44 |
| Std. Dev. of RLU/CO | | 0.85 | 3.29 | 0.11 | 1.27 | 0.17 | 1.60 | 10.15 | 6.38 |
| Fold increase | | 1.00 | 3.03 | 0.39 | 1.49 | 0.33 | 3.01 | 6.74 | |

Example 6

This example shows that the compositions and methods disclosed herein can be used with biological samples preserved using either cross-linking fixatives or precipitating fixatives.

Two types of liquid cryological preservative media are commonly used to preserve clinical cervical samples: SUREPATH, which is an aldehyde-based fixative; and PRESERVCYT, which is a methanol-based fixative. Methods have been developed for testing such samples for HPV DNA, the presence of which is indicative of an active HPV infection. Previously, no uniform method had been developed that is useful for both SUREPATH and PRESERVCYT-fixed clinical cervical samples.

The presently-disclosed methods and compositions were tested for their utility in detecting HPV DNA in samples fixed in either SUREPATH or PRESERVCYT.

SiHa cells are a squamous cell carcinoma cell line derived from a patient having grade II cervical tumor. SiHa cells have been shown to contain an integrated HPV-type 16 genome and thus provide a useful positive control for the extraction and detection of HPV DNA.

SiHa cells were spiked into an HPV-negative clinical specimen pool and preserved in either SUREPATH or PRESERVCYT. The same volume of HPV-negative clinical specimen pool lacking SiHa cells were used as controls. Each sample was pelleted by centrifugation and the supernatant decanted.

One set of each sample was then extracted using a commercially available method by suspending the cell pellet in 50 μL Specimen Transport Medium comprising guanidine hydrochloride and 25 μL of Denaturation Regent comprising NaOH and then lysed at 65° C. for 90 min.

A second set of each sample was resuspended in deionized water. 3% (v/v/) Brij-58, 150 mM Tris, 150 mM diethanolamine, DNA binding magnetic beads, and Proteinase K were added to the suspension and the sample was then lysed at 68.5° C. for 7.5 minutes and then 60° C. for 12.5 minutes. A magnetic field was applied to separate the beads from the solution, then the beads were washed, and DNA eluted.

Figure 6:
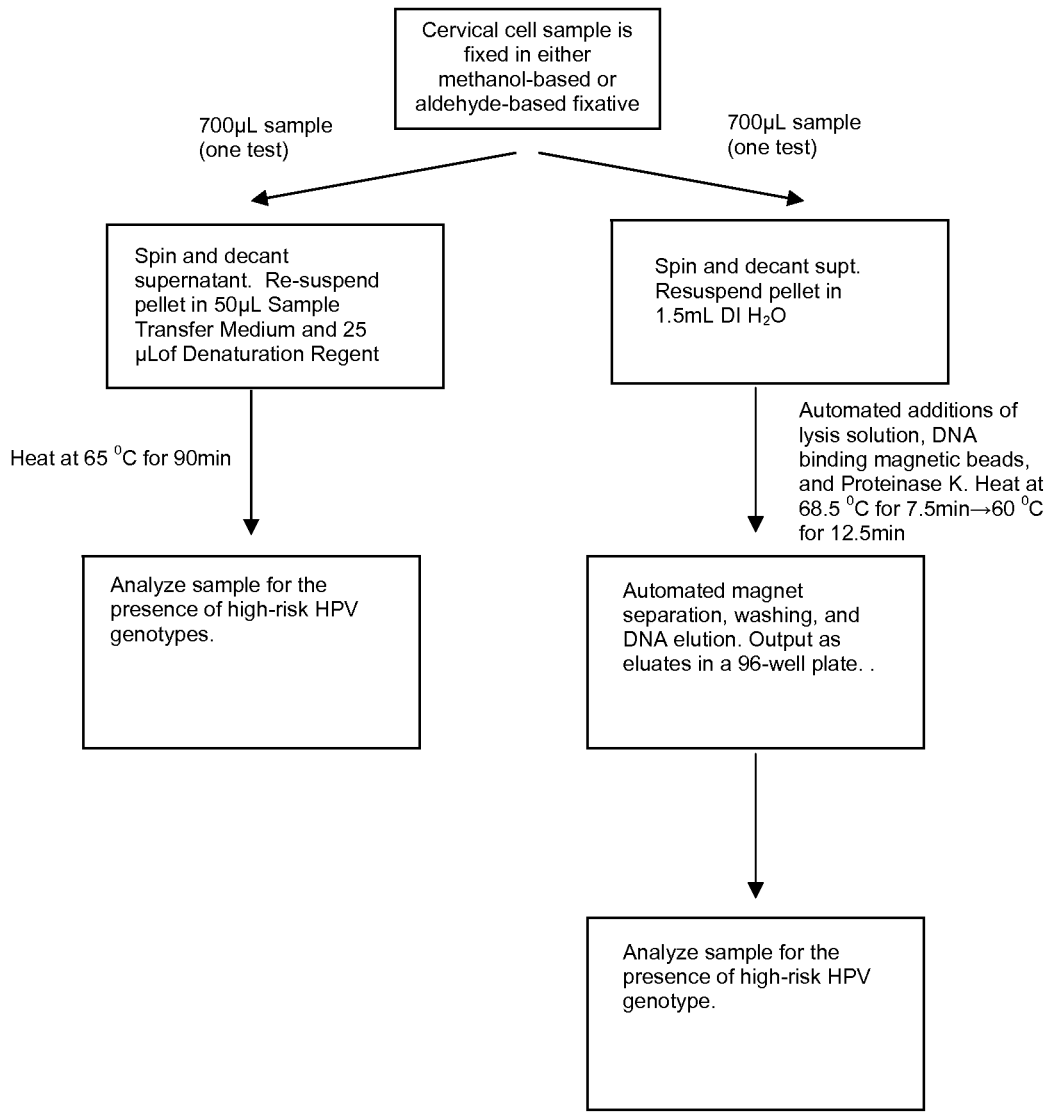
FIG. 6 is a flow chart showing the protocols used for determining the usefulness of lysis solutions in both manual and automated extraction of nucleic acid from either alcohol-based or aldehyde-based lysis buffers. The left branch of the flow chart shows a manual method, while the right branch shows an automated method using magnetic beads.
Figure 7:
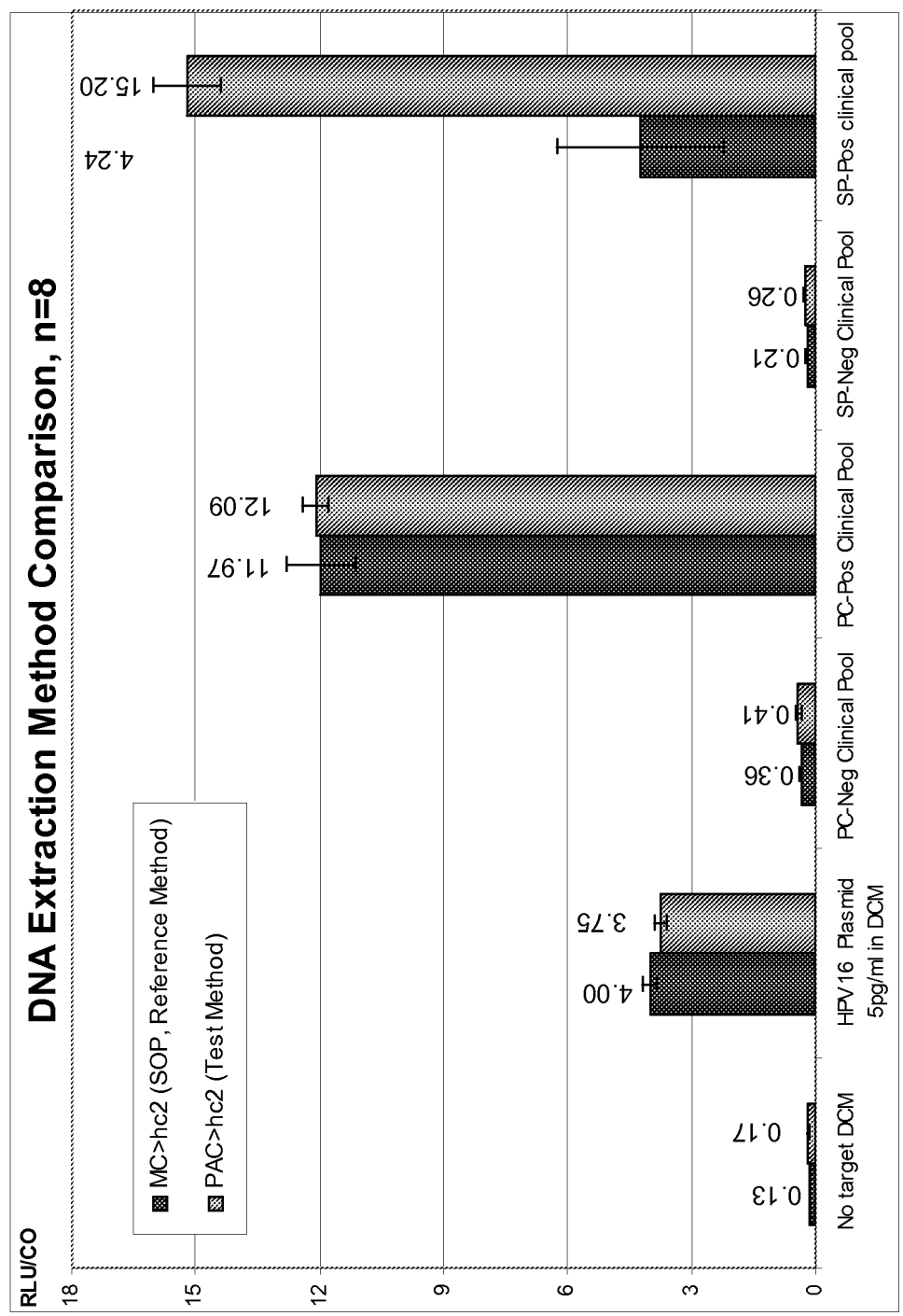
FIG. 7 shows the effectiveness of extracting nucleic acids using two types of lysis solutions. "MC" indicates manual conversion of the samples, as is currently performed with liquid based cytology samples and as indicated in FIG. 6. "PAC" indicates pre-analytic chemistry. "PC-Neg Clinical Pool" indicates HPV-negative cervical clinical samples that have been fixed with PRESERVCYT liquid cytological preservation media. "PC-Pos Clinical Pool" indicates HPV-negative cervical clinical samples that have been spiked with HPV-positive SiHa cells and fixed with PRESERVCYT liquid cytological preservation media. "SP-Neg Clinical Pool" indicates HPV-negative cervical clinical samples that have been fixed with SUREPATH liquid cytological preservation media. "SP-Pos Clinical Pool" indicates HPV-negative cervical clinical samples that have been spiked with HPV-positive SiHa cells and fixed with SUREPATH liquid cytological preservation media. A negative control containing only Digene Collection Medium and a positive control containing HPV16 plasmid suspending in Digene Collection Medium also were tested.
Figure 8A:
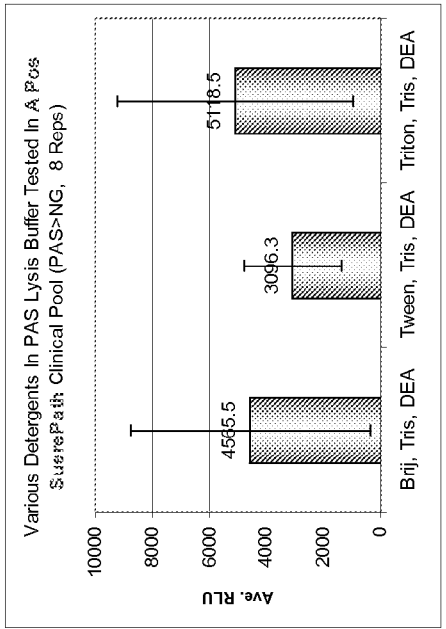
FIGS. 8A to 8D show the effect of varying the detergent on extraction and detection of HPV DNA in samples preserved in PRESERVCYT or SUREPATH.
Figure 8B:
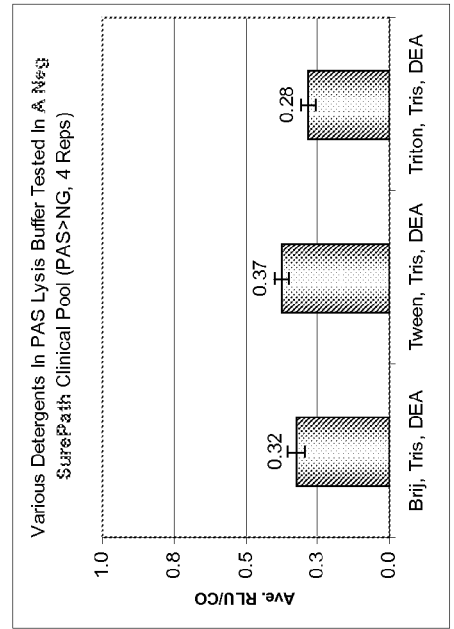
Figure 8C:
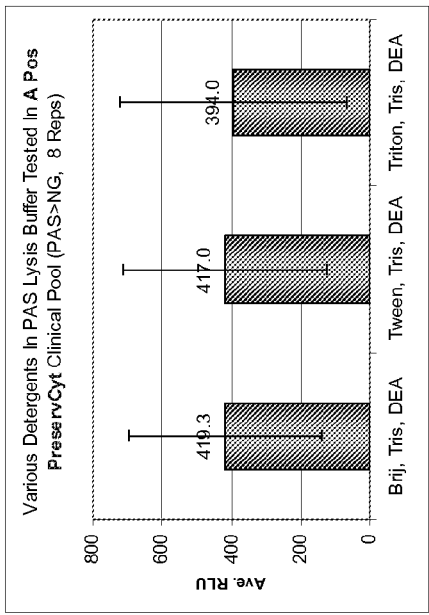
Figure 8D:
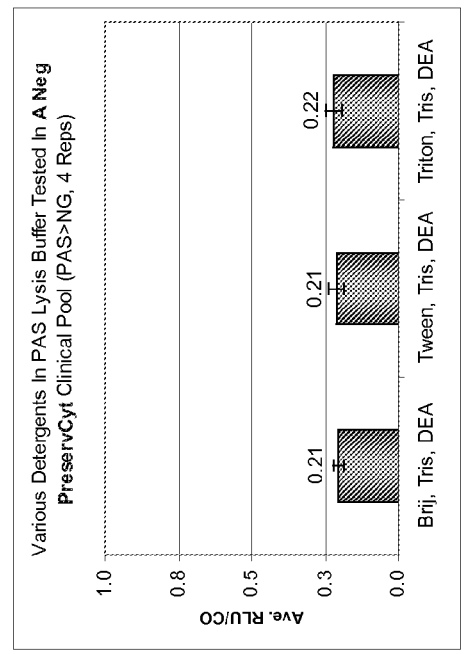

DNA eluates generated by both methods then were then tested side-by-side by a hybrid capture method. Recovery was determined by signal output from each method. A flow chart outlining the two methods can be seen at FIG. 6. Results can be seen at FIG. 7. In PRESERVCYT samples, both recovery methods displayed a similar degree of DNA recovery. In SUREPATH samples, on the other hand, use of a Brij-58/Tris/diethanolamine lysis solution resulted in a 3.5 fold increase in signal compared with the standard lysis solution.

Various detergents also were tested in these methods. SiHa cells were spiked into an HPV-negative clinical specimen pool and preserved in either SUREPATH or PRESERVCYT. The same volume of HPV-negative clinical specimen pool lacking SiHa cells were used as controls. Each sample was pelleted by centrifugation at and the supernatant decanted. The cell pellet was then resuspended in 1.5 mL of deionized water. A lysis solution comprising 150 mM Tris, 150 mM diethanolamine, and a detergent chosen from 3% (v/v) Brij-58, Tween-20, and TRITON X-100) was used. Typically, 1.5 mL of the sample is added to 1 mL of lysis buffer, plus 25 μl of Proteinase K (10 mg/ml stock) and 60 μl of 1.5% (v/v) AxpH™ DNA-affinity magnetic beads to lyse. The sample was then lysed at 68.5° C. for 7.5 minutes and then 60° C. for 12.5 min. A magnetic field was applied to separate the beads from the solution, the beads were washed, and DNA eluted.

Results are shown at FIGS. 8A to 8D. As can be seen, there is no significant difference in the amount DNA recovered based on the identity of the detergent.

What is claimed is:

1. A method of lysing a fixed biological sample, the method comprising lysing the fixed biological sample with a composition comprising at least two amines, wherein the method is useful for both aldehyde-based fixatives and alcohol-based fixatives, and wherein the pH of the composition is 8 or greater.

2. A method of isolating a component of a fixed biological sample, the method comprising:
   a. lysing the fixed biological sample according to the method of claim 1; and
   b. isolating the component from the lysate.

3. The method of claim 2, wherein at least one of the amines is selected from the group consisting of methylamine, dimethylamine, diethylamine, trimethlylamine, triethylamine, monoethanolamine, diethanolamine, triethanolamine, ethylenediamine, diethylenetriamine, tris(hydroxymethyl)aminomethane, hexamethylenetetramine, aniline, and an amino acid.

4. The method of claim 2, wherein at least one of the amines is a buffering agent.

5. The method of claim 4, wherein the buffering agent is selected from the group consisting of tris(hydroxymethyl)aminomethane ("TRIS"), N-tris-(hydroxymethyl)methyl-3-aminopropanesulfonic acid ("TAPS"), 3-[N-tris-(hydroxymethyl)-methyl-amino]-2-hydroxypropanesulfonic acid ("TAPSO"); N-tris(hydroxymethyl)methyl-2-am inoethanesulfonic acid ("TES"); N-[tris(hydroxymethyl)methyl]-glycine ("TRICINE"); bis(2-hydroxyethyl)iminotris-(hydroxymethyl)methane ("bis-TRIS"); and 1,3-bis[tris(hydroxy-methyl)methylamino]propane ("bis-TRIS PROPANE").

6. The method of claim 4, wherein the buffering agent is TRIS.

7. The method of claim 2, wherein at least one of the amines is diazoamine.

8. The method of claim 2, wherein the composition further comprises at least one detergent.

9. The method of claim 8, wherein the detergent is selected from the group consisting of polyoxyethyleneglycol dodecyl ether, 3-[(3-cholamidopropyl)dimethylammonio]-1-propanesulfonate, tert-octylphenoxy poly(oxyethylene)ethanol (NONIDET P-40), Igepal CA-630, deoxycholate, 4-(1,1,3,3-Tetramethylbutyl)phenyl-polyethylene glycol (TRITON X-100), sodium dodecyl sulfate, and polysorbate surfactants.

10. The method of claim 2, wherein the composition further comprises at least one DNA-binding magnetic bead.

11. The method of claim 2, wherein the composition comprises:
   150 mM Tris-HCl;
   300 mM diethanolamine;
   3% Brij-58;
   0.09% sodium azide; and
   wherein the composition has a pH of approximately 9.4.

12. The method of claim 1, wherein the fixed biological sample is fixed with a cross-linking fixative agent.

13. The method of claim 12, wherein the cross-linking fixative agent comprises an aldehyde.

14. The method of claim 13, wherein the aldehyde is selected from the group consisting of formaldehyde and glutaraldehyde.

15. The method of claim 1, wherein the fixed biological sample is fixed with a fixative agent comprising an alcohol.

16. The method of claim 15, wherein the alcohol is selected from the group consisting of methanol and ethanol.

17. The method of claim 1, wherein the fixed biological sample is fixed with a fixative agent selected from the group consisting of the aldehyde-based cytology medium SURE-PATH™, and the alcohol-based cytology medium PRESERVCYT™.

18. The method of claim 1, wherein the fixed biological sample is a cervical sample.

19. The method of claim 2, wherein the component is a nucleic acid molecule.

20. The method of claim 19, wherein the nucleic acid molecule comprises a specific sequence.

21. The method of claim 20, wherein the nucleic acid is isolated according to a method comprising hybridizing a nucleic acid probe to the specific sequence of the nucleic acid molecule.

22. The method of claim 21, wherein the nucleic acid probe is adapted to be bound to a solid phase or is bound to a solid phase.

23. The method of claim 22, wherein the solid phase is a magnetic bead.

24. The method of claim 21, wherein the hybridizing of the nucleic acid probe to the specific sequence of the nucleic acid molecule results in the formation of a DNA:RNA hybrid between the nucleic acid molecule and the nucleic acid probe.

25. The method of claim 24, wherein the DNA:RNA hybrid is bound by a DNA:RNA hybrid-binding antibody.

26. The method of claim 25, wherein the DNA:RNA hybrid-binding antibody is bound to a solid phase or adapted to be bound to a solid phase.

27. The method of claim 26, wherein the solid phase is a magnetic bead.

28. The method of claim 19, wherein the nucleic acid molecule is a viral nucleic acid molecule.

29. The method of claim 2, wherein the fixed biological sample is a cervical sample.

30. The method of claim 9, wherein the detergent is deoxycholate, 4-(1,1,3,3-Tetramethylbutyl)phenyl-polyethylene glycol (TRITON X-100).

31. The method of claim 2, wherein the composition comprises Tris-HCl, diethanolamine, Brij-58, and sodium azide.

32. The method of claim 31, wherein the composition has a pH of approximately 9.4.

33. The method of claim 31, wherein the amount of each of Tris-HCl and diethanolamine is about 150 mM or greater.

* * * * *